US008435539B2

(12) United States Patent
McBride et al.

(10) Patent No.: US 8,435,539 B2
(45) Date of Patent: May 7, 2013

(54) DELIVERY SYSTEM FOR CYTOTOXIC DRUGS BY BISPECIFIC ANTIBODY PRETARGETING

(75) Inventors: William J. McBride, Boonton, NJ (US);
Christopher A. D'Souza, Pomona, NY (US); Chien-Hsing Chang, Downingtown, PA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 25 days.

(21) Appl. No.: 12/964,132

(22) Filed: Dec. 9, 2010

(65) Prior Publication Data

US 2011/0076233 A1    Mar. 31, 2011

Related U.S. Application Data

(60) Continuation-in-part of application No. 12/949,536, filed on Nov. 18, 2010, now Pat. No. 8,211,440, which is a division of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. 11/391,584, filed on Mar. 28, 2006, now Pat. No. 7,521,056, application No. 12/964,132, which is a continuation-in-part of application No. 12/915,515, filed on Oct. 29, 2010, and a continuation-in-part of application No. 12/871,345, filed on Aug. 30, 2010, and a continuation-in-part of application No. 12/869,823, filed on Aug. 27, 2010, and a continuation-in-part of application No. 12/754,740, filed on Apr. 6, 2010, and a continuation-in-part of application No. 12/752,649, filed on Apr. 1, 2010, now Pat. No. 8,034,352, and a continuation-in-part of application No. 12/731,781, filed on Mar. 25, 2010, now Pat. No. 8,003,111, and a continuation-in-part of application No. 12/644,146, filed on Dec. 22, 2009, now Pat. No. 7,981,398, which is a division of application No. 11/925,408, filed on Oct. 26, 2007, now Pat. No. 7,666,400, application No. 12/964,132, which is a continuation-in-part of application No. 12/544,476, filed on Aug. 20, 2009, now Pat. No. 7,901,680, and a continuation-in-part of application No. 12/468,589, filed on May 19, 2009, now Pat. No. 8,163,291, which is a division of application No. 11/389,358, filed on Mar. 24, 2006, now Pat. No. 7,550,143, application No. 12/964,132, which is a continuation-in-part of application No. 12/418,877, filed on Apr. 6, 2009, now Pat. No. 7,906,118, and a continuation-in-part of application No. 12/417,917, filed on Apr. 3, 2009, now Pat. No. 7,906,121, which is a division of application No. 11/478,021, filed on Jun. 29, 2006, now Pat. No. 7,534,866, application No. 12/964,132, which is a division of application No. 12/396,965, filed on Mar. 3, 2009, now Pat. No. 7,871,622.

(60) Provisional application No. 60/864,530, filed on Nov. 6, 2006, provisional application No. 61/258,369, filed on Nov. 5, 2009, provisional application No. 61/258,729, filed on Nov. 6, 2009, provisional application No. 61/378,059, filed on Aug. 30, 2010, provisional application No. 61/238,473, filed on Aug. 31, 2009, provisional application No. 61/266,305, filed on Dec. 3, 2009, provisional application No. 61/316,996, filed on Mar. 24, 2010, provisional application No. 61/323,960, filed on Apr. 14, 2010, provisional application No. 61/238,424, filed on Aug. 31, 2009, provisional application No. 61/168,290, filed on Apr. 10, 2009, provisional application No. 61/168,657, filed on Apr. 13, 2009, provisional application No. 61/168,668, filed on Apr. 13, 2009, provisional application No. 61/163,666, filed on Mar. 26, 2009, provisional application No. 60/668,603, filed on Apr. 6, 2005, provisional application No. 61/090,487, filed on Aug. 20, 2008, provisional application No. 61/043,932, filed on Apr. 10, 2008, provisional application No. 61/104,916, filed on Oct. 13, 2008, provisional application No. 61/119,542, filed on Dec. 3, 2008.

(51) Int. Cl.
*A61K 39/385* (2006.01)
*A61K 51/08* (2006.01)
*A61K 38/04* (2006.01)
*C08G 59/00* (2006.01)
*C07B 41/08* (2006.01)

(52) U.S. Cl.
USPC ... 424/193.1; 424/1.37; 424/1.53; 424/78.18; 530/327; 530/363; 528/403

(58) Field of Classification Search ............. None
See application file for complete search history.

(56) References Cited

U.S. PATENT DOCUMENTS

| | | |
|---|---|---|
| 4,046,722 A | 9/1977 | Rowland |
| 4,699,784 A | 10/1987 | Shih et al. |
| 4,818,709 A | 4/1989 | Primus et al. |
| 4,868,109 A | 9/1989 | Lansdorp et al. |
| 5,194,254 A | 3/1993 | Barber et al. |
| 5,478,556 A | 12/1995 | Elliot et al. |
| 5,530,101 A | 6/1996 | Queen et al. |
| 5,571,515 A | 11/1996 | Scott et al. |
| 5,585,089 A | 12/1996 | Queen et al. |
| 5,614,610 A | 3/1997 | Hellstrom et al. |
| 5,693,762 A | 12/1997 | Queen et al. |
| 5,770,198 A | 6/1998 | Coller et al. |
| 5,789,554 A | 8/1998 | Leung et al. |
| 5,798,100 A | 8/1998 | Hansen |
| 5,859,205 A | 1/1999 | Adair et al. |
| 5,874,540 A | 2/1999 | Hansen et al. |
| 6,132,718 A | 10/2000 | Hansen |
| 6,180,370 B1 | 1/2001 | Queen et al. |
| 6,180,377 B1 | 1/2001 | Morgan et al. |
| 6,187,287 B1 | 2/2001 | Leung et al. |
| 6,261,537 B1 | 7/2001 | Klaveness |
| 6,306,393 B1 | 10/2001 | Goldenberg et al. |
| 6,416,958 B2 | 7/2002 | Vidovic et al. |
| 6,440,416 B1 | 8/2002 | Hansen et al. |

| | | | |
|---|---|---|---|
| 6,524,854 | B1 | 2/2003 | Mania et al. |
| 6,617,135 | B1 | 9/2003 | Gillies et al. |
| 6,730,300 | B2 | 5/2004 | Leung et al. |
| 6,894,149 | B2 | 5/2005 | Tso et al. |
| 6,926,893 | B1 | 8/2005 | Hansen |
| 7,022,500 | B1 | 4/2006 | Queen et al. |
| 7,052,872 | B1 | 5/2006 | Hansen et al. |
| 7,060,506 | B2 | 6/2006 | Craig |
| 7,151,164 | B2 | 12/2006 | Hansen et al. |
| 7,262,278 | B2 | 8/2007 | Tawara et al. |
| 7,312,318 | B2 | 12/2007 | Hansen et al. |
| 7,354,587 | B1 | 4/2008 | Hansen |
| 7,432,342 | B2 | 10/2008 | Braun et al. |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,541,440 | B2 | 6/2009 | Goldenberg et al. |
| 7,550,143 | B2 | 6/2009 | Chang et al. |
| 7,591,994 | B2 | 9/2009 | Govindan et al. |
| 7,666,400 | B2 | 2/2010 | Chang et al. |
| 2003/0103979 | A1 | 6/2003 | Leung et al. |
| 2003/0198956 | A1 | 10/2003 | Makowski et al. |
| 2003/0228326 | A1 | 12/2003 | Palomba et al. |
| 2003/0232420 | A1 | 12/2003 | Braun et al. |
| 2004/0018587 | A1 | 1/2004 | Makowski et al. |
| 2005/0003403 | A1 | 1/2005 | Rossi et al. |
| 2006/0210475 | A1 | 9/2006 | Goldenberg et al. |
| 2006/0228300 | A1 | 10/2006 | Chang et al. |
| 2006/0228357 | A1 | 10/2006 | Chang et al. |
| 2007/0020259 | A1 | 1/2007 | Hansen et al. |
| 2007/0086942 | A1 | 4/2007 | Chang et al. |
| 2007/0140966 | A1 | 6/2007 | Chang et al. |
| 2007/0264265 | A1 | 11/2007 | Goldenberg et al. |
| 2008/0015157 | A1 | 1/2008 | Umeda et al. |
| 2009/0060862 | A1 | 3/2009 | Chang et al. |
| 2009/0111143 | A1 | 4/2009 | Goldenberg et al. |
| 2009/0202433 | A1 | 8/2009 | Chang et al. |
| 2009/0202487 | A1 | 8/2009 | Chang et al. |
| 2009/0304580 | A1 | 12/2009 | Goldenberg et al. |
| 2010/0068137 | A1 | 3/2010 | Chang et al. |
| 2010/0189641 | A1 | 7/2010 | Chang et al. |
| 2010/0189689 | A1 | 7/2010 | Chang et al. |
| 2010/0196266 | A1 | 8/2010 | Goldenberg et al. |

FOREIGN PATENT DOCUMENTS

| | | | |
|---|---|---|---|
| EP | 0324625 | A1 | 7/1989 |
| EP | 0340793 | B1 | 8/1995 |
| EP | 0438803 | B1 | 3/1997 |
| EP | 0306995 | B1 | 4/1997 |
| WO | 91/11465 | A1 | 8/1991 |
| WO | 92/15322 | A1 | 9/1992 |
| WO | 93/11162 | A1 | 6/1993 |
| WO | 94/05329 | A1 | 3/1994 |
| WO | 96/04313 | A1 | 2/1996 |
| WO | 96/37224 | A1 | 11/1996 |
| WO | 96/40941 | A1 | 12/1996 |
| WO | WO0068248 | | 11/2000 |
| WO | 2006/107617 | | 10/2006 |
| WO | 2006/107786 | | 10/2006 |
| WO | WO 2007/080114 | * | 7/2007 |
| WO | WO2007075270 | | 7/2007 |
| WO | 2008/033413 | | 3/2008 |

OTHER PUBLICATIONS

Moon et al, J Med Chem 51(21): 6916-6926, Nov. 13, 2008.*
Abbas et al., Cellular and Molecular Immunology, W.B. Saunders Company, 1991, p. 43.
Alto et al., "Bioinformatic design of A-kinase anchoring protein-in silico: A potent and selective peptide antagonist of type II protein kinase A anchoring", PNAS USA 100:4445-50, 2003.
Backer et al., "Self-Assembled "Dock and Lock" System for Linking Payloads to Targeting Proteins", Bioconjugate Chem., 17 (4), pp. 912-919, 2006.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.

Goldenberg et al., "Properties and structure-function relationships of veltuzumab (hA20), a humanized anti-CD20 monoclonal antibody" Blood 113:1062-70 (2009).

Goodson et al., "Site-Directed PEGylation of Recombinant Interleukin-2 at its Glycosylation Site", Nat. Biotechnology Apr. 1990;8(4):343-6.

Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.

Grimley et al., "Prolonged STAT1 Activation Related to the Growth Arrest of Malignant Lymphoma Cells by Interferon-α" Blood 91(8):3017-27 (1998).

Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).

Gutterman et al., "Cytokine therapeutics: Lessons from interferon α" Proc. Natl. Acad. Sci. USA 91:1198-205 (1994).

Harris et al., "Effect of pegylation on pharmaceuticals" Nat. Rev. Drug. Discov. 2:214-221 (2003).

Hausken et al. "Mutational Analysis of the A-Kinase Anchoring Protein (AKAP)-binding Site on RII", J. Biol. Chem. 271:29016-22 (1996).

Hodneland et al., "Selective immobilization of proteins to self-assembled monolayers presenting active site-directed capture ligands", Proc. Natl. Acd. Sci. USA 2002; 99:5048-5052.

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7δ-protein kinase A interaction yields novel protein kinase A-anchoring disruptor peptides" Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF" Pharm. Res. 1996;13 (7):996-1002.

Kramer et al., "Cell and virus sensitivity studies with recombinant human alpha interferons" J. Interferon. Res. 3 (4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).

Luft et al., "Type I IFNs Enhance the Terminal Differentiation of Dendritic Cells" J. Immunol. 161:1947-1953 (1998).

Mason, Anthony J., "Functional Analysis of the Cysteine Residues of Activin A", Mol. Endocrinol. 8:325-32, 1994.

Matarrese et al., "Type I Interferon Gene Transfer Sensitizes Melanoma Cells to Apoptosis via a Target Activity on Mitochondrial Function" Am. J. Pathol. 2002, 160(4):1507-1520.

Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.

Newlon et al., "A Novel Mechanism of PKA Anchoring Revealed by Solution Structures of Anchoring Complexes", EMBO J. 2001; 20:1651-1662.

Newlon et al., "The molecular basis for protein kinase A anchoring revealed by solution NMR", Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.

Nordstrom et al., "First Bispecific Antibody Immunocytokine (Anti-CD20/HLA-DR-Interferon-α2b) is Highly Toxic for Human Lymphoma Cells in Vitro", 2009 ASH Annual Meeting Abstracts, Nov. 20, 2009; 114(22):675, Abstract #1695.

Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).

Oyen et al., "Human testis cDNA for the regulatory subunit RIIα of cAMP-dependent protein kinase encodes an alternate amino-terminal region", FEBS Letters 246:57-64, 1989.

Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-137 (1998).

Paquette et al., "Interferon-α and granulocyte-macrophage colony-stimulating factor differentiate peripheral blood monocytes into potent antigen-presenting cells" J. Leukoc. Biol. 64:358-367; 1998.

Pelham et al., "Interferon-α conjugation to human osteogenic sarcoma monoclonal antibody 791T/36" Cancer Immunol. Immuother. 1983;15(3):210-216.

Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.

Pilling et al., "Interferon-β mediates stromal cell rescue of T cells from apoptosis" Eur. J. Immunol. 29:1041-1050 (1999).

Rabjohn et al., "Molecular Cloning and Epitope Analysis of the Peanut Allergen Ara h 3" J. Clinical Investigation 103 (4):535-542 (1999).

Raefsky et al., "Studies of Interferon as a regulator of hematopoietic cells proliferation" J. Immunol. 135 (4):2507-2512 (1985).

Rose et al., "Structural basis of dimerization, coactivator recognition and MODY3 mutations in HNF-1α", Nature Struct. Biol. 2000; 7:744-748.

Rosendahl et al., "A Long-Acting, Highly Potent Interferon α-2 Conjugate Created Using Site-Specific PEGylation" Bioconjugate Chem. 2005;16:200-207.

Rossi et al., "Novel Designs of Multivalent Anti-CD20 Humanized Antibodies as Improved Lymphoma Therapeutics", Cancer Res. 68:8384-92, 2008.

Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.

Rossi et al., "CD20-targeted tetrameric interferon-α, a novel and potent immunocytokine for the therapy of B-cell lymphomas", Blood 2009;114:3864-3871.

Rossi et al., "A veltuzumab-IFNα2b conjugate with potent in vitro and in vivo anti-lymphoma activity", Proceedings of the American Association for Cancer Research, Apr. 2009;50:783-784, Abstract # 3237.

Rustandi et al., "The Ca2+-Dependent Interaction of S100B(ββ) with a Peptide Derived from p53", Biochemistry 1998; 37: 1951-1960.

Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.

Salles et al., "Rituximab combined with chemotherapy and interferon in follicular lymphoma patients: results of the GELA-GOELAMS FL2000 study" Blood 2008; 112:4824-4831.

Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).

Scott et al., "Type II Regulatory Subunit Dimerization Determines the Subcellular Localization of the cAMP-dependent Protein Kinase", J. Biol. Chem. 265:21561-66 (1990).

Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).

Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Sidky et al., "Inhibition of Angiogenesis by Interferons: Effects on Tumor- and Lymphocyte-induced Vascular Responses" Cancer Res. 47:5155-5161, Oct. 1, 1987.

Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.

Stein et al., "Characterization of a humanized IgG4 anti-HLA-DR monoclonal antibody that lacks effector cell functions but retains direct antilymphoma activity and increases the potency of rituximab" Blood 2006;108:2736-2744.

Stokka et al., "Characterization of A-kinase-anchoring disruption using a solution-based assay" Biochem. J. (2006) 400, 493-499.

Stryer et al., "Levels of Structure in Protein Architecture", Biochemistry, 3rd Ed., pp. 31-33, W.H. Freeman & Co., New York, 1988.

Takaoka et al., "Integration of interferon-α/β signalling to p53 responses in tumour suppression and antiviral defence" Nature Jul. 31, 2003;424(6948):516-23.

Taylor, S., "cAMP-dependent Protein Kinase" J. Biol. Chem. 1989;264(15):8443-8446.

Walsh et al., "An Adenosine 3', 5'-Monophosphate-dependant Protein Kinase from Rabbit Skeletal Muscle" J. Biol. Chem. 243(13):3763-3774 (1968).

Weck et al., "Comparison of the Antiviral Activities of Various Cloned Human Interferon-α Subtypes in Mammalian Cell Cultures" J. Gen. Virol. (1981), 57, 233-237.

Winkler et al., "Changing the Antigen Binding Specificity by Single Point Mutations of an Anti-p24 (HIV-1) Antibody", J. Immunol. 165:4505-14, 2000.

Witkowski et al., "Conversion of a β-Ketoacyl Synthase to a Malonyl Decarboxylase by Replacement of the Active-Site Cysteine with Glutamine" Biochemistry 38(36):11643-50 (1999).

Wong et al., "AKAP Signalling Complexes: Focal Points in Space and Time", Nat. Rev. Mol. Cell Biol. 12:959-70 (2004).

Zhu et al., "Inhibition of tumor growth and metastasis by targeting tumor-associated angiogenesis with antagonists to the receptors of vascular endothelial growth factor", Invest. New Drugs 17:195-212, 1999.

Belyakov et al., "Shared modes of protection against poxvirus infection by attenuated and conventional smallpox vaccine viruses", Proc Natl Acad Sci U S A. Aug. 5, 2003;100(16):9458-63. Epub Jul. 17, 2003.

Berhanu et al., "Vaccination of BALB/c mice with *Escherichia coli*-expressed vaccinia virus proteins A27L, B5R, and D8L protects mice from lethal vaccinia virus challenge", J Virol. Apr. 2008;82(7):3517-29. Epub Jan. 16, 2008.

Born et al., "A poxvirus protein that binds to and inactivates IL-18, and inhibits NK cell response", J Immunol. Mar. 15, 2000;164(6):3246-54.

Carayanniotis et al., "Characterization of the adjuvant-free serological response to protein antigens coupled to antibodies specific for class II MHC determinants", Vaccine. Apr. 1990;8(2):137-44.

Chung et al., "A27L protein mediates vaccinia virus interaction with cell surface heparan sulfate", J Virol. Feb. 1998;72(2):1577-85.

Ding et al., "Targeting of antigens to B cells augments antigen-specific T-cell responses and breaks immune tolerance to tumor-associated antigen MUC1", Blood. Oct. 1, 2008;112(7):2817-25. Epub Jul. 31, 2008.

Grandpre et al., "Immunogenicity of recombinant Modified Vaccinia Ankara following a single or multi-dose vaccine regimen in rhesus monkeys", Vaccine. Mar. 4, 2009;27(10):1549-56. Epub Jan. 23, 2009.

He et al., "Antibodies to the A27 protein of vaccinia virus neutralize and protect against infection but represent a minor component of Dryvax vaccine—induced immunity", J Infect Dis. Oct. 1, 2007;196(7):1026-32. Epub Aug. 20, 2007.

Hsiao et al., "Vaccinia virus envelope D8L protein binds to cell surface chondroitin sulfate and mediates the adsorption of intracellular mature virions to cells", J Virol. Oct. 1999;73(10):8750-61.

Jackson et al., "Role of genes that modulate host immune responses in the immunogenicity and pathogenicity of vaccinia virus", J Virol. May 2005;79(10):6554-9.

Kan-Mitchell et al., "The HIV-1 HLA-A2-SLYNTVATL is a help-independent CTL epitope", J Immunol. May 1, 2004;172(9):5249-61.

Kretz-Rommel et al., "In vivo targeting of antigens to human dendritic cells through DC-SIGN elicits stimulatory immune responses and inhibits tumor growth in grafted mouse models", J Immunother. Oct. 2007;30(7):715-26.

Livingston et al., "A rational strategy to design multiepitope immunogens based on multiple Th lymphocyte epitopes", J Immunol. Jun. 1, 2002;168(11):5499-506.

O'Neill et al., "Exploiting dendritic cells for active immunotherapy of cancer and chronic infections", Mol Biotechnol. Jun. 2007;36(2):131-41.

Pien et al., "A unique mechanism for innate cytokine promotion of T cell responses to viral infections", J Immunol. Nov. 15, 2002;169(10):5827-37.

Rosenthal et al., "Developing new smallpox vaccines", Emerg Infect Dis. Nov.-Dec. 2001;7(6):920-6.

Scott et al., "IFN-gamma modulates the early development of Th1 and Th2 responses in a murine model of cutaneous leishmaniasis", J Immunol. Nov. 1, 1991;147(9):3149-55.

Tacken et al., "Dendritic-cell immunotherapy: from ex vivo loading to in vivo targeting", Nat Rev Immunol. Oct. 2007;7 (10):790-802.

Tew et al., "Follicular dendritic cells and presentation of antigen and costimulatory signals to B cells", Immunol Rev. Apr. 1997;156:39-52.

Vulink et al., "Dendritic cells in cancer immunotherapy", Adv Cancer Res. 2008;99:363-407.

Xiang et al., "IL-18 binding and inhibition of interferon gamma induction by human poxvirus-encoded proteins", Proc Natl Acad Sci U S A. Sep. 28, 1999;96(20):11537-42.

Xu et al., "The orthopoxvirus type I IFN binding protein is essential for virulence and an effective target for vaccination", J Exp Med. Apr. 14, 2008;205(4):981-92. Epub Apr. 7, 2008.

Amigorena et al., "Transient accumulation of new class II MHC molecules in a novel endocytic compartment in B lymphocytes" Nature 369:113-120 (1994).

Becker et al., "Expression of a Hybrid Immunoglobulin-T Cell Receptor Protein in Transgenic Mice", Cell, 58:911-921 (Sep. 1989).

Becker, S., "Inteferon-γ Accelerates Immune Proliferation via Its Effect on Monocyte HLA-DR Expression", Cell. Immunol. Mar. 1985;91(1):301-7.

Bohlen et al., "Idiotype vaccination strategies against a murine B-cell lymphoma: Dendritic cells loaded with idiotype and bispecific idiotype x anti-class II antibodies can protect against tumor growth", Cytokines Mol. Ther. Dec. 1996;2 (4):231-8.

Bolhuis et al., "T Cell Targeting in Cancer Therapy", Cancer Immunol. Immunother., 34:1-8 (1991).

Bolhuis et al., "Engineering T Lymphocyte Antigen Specificity", J. Cell. Biochem. 47:306-310, (1991).

Bremnes et al., "An LI and ML motif in the cytoplasmic tail of the MHC-associated invariant chain mediate rapid internalization", J. Cell. Science 107:2021-2032 (1994).

Burnett et al., "Human Monoclonal Antibodies to Defined Antigens", Human Hybridomas & Monoclonal Antibodies (Engelman et al, eds.) Plenum Press, New York, 1985, pp. 114-115.

Carayanniotis et al., "Delivery of synthetic peptides by anti-class II MHC monovalent antibodies induces specific adjuvant-free IgG responses in vivo", Mol. Immunol. 25(9):907-911 (1988).

Chen et al., "Novel strategies for improved cancer vaccines", Expert Rev. Vaccines 8(5):567-76 (2009).

Cohen et al., "Cancer Vaccines Get a Shot in the Arm", Science 262:841-843 (1993).

Durrant et al., "An idiotypic replica of carcinoembryonic antigen inducing cellular and humoral responses directed against human colorectal tumours", Int. J. Cancer 50:811-816 (1992).

Eshhar et al., "Chimeric T cell receptor which incorporates the antitumour specificity of a monoclonal antibody with the cytolytic activity of T cells: a model system for immunotherapeutical approach", Br. J. Cancer 62:27-29, 1990.

Eshhar et al., "Specific activation and targeting of cytotoxic lymphocytes through chimeric single chains consisting of antibody-binding domains and the γ or ζ subunits of the immunoglobulin and T-cell receptors", Proc. Natl. Acad. Sci. USA, 90:720-724 (1993).

Fagerberg et al., "Induction of an immune network cascade in cancer patients treated with monoclonal antibodies (ab1)", Cancer Immunol. Immunother. 37:264-270 (1993).

Fong et al., "Dendritic cell-based xenoantigen vaccination for prostate cancer immunotherapy", J. Immunol. 167 (12):7150-6 (2001).

Goldenberg et al., "Monoclonal Antibodies in Cancer Detection and Therapy", Am. J. Med. 94(3):297-312 (1993).

Goldenberg et al., "New Developments in Monoclonal Antibodies for Cancer Detection and Therapy", CA Cancer J. Clin. 44(1):43-64 (1994).

Goverman et al., "Chimeric immunoglobulin-T cell receptor proteins form functional receptors: implications for T cell receptor complex formation and activation", Cell 60:929-939 (1993).

Gross et al., "Generation of effector T cells expressing chimeric T cell receptor with antibody type-specificity", Transp. Proc. 21(1):127-130 (Feb. 1989).

Gross et al., "Expression of immunoglobulin-T-cell receptor chimeric molecules as functional receptors with antibody-type specificity", Proc. Natl. Acad. Sci. USA 86:10024-10028 (Dec. 1989).

Hefta et al., "Expression of Carcinoembryonic Antigen and Its Predicted Immunoglobulin-like Domains in HeLa Cells for Epitope Analysis", Cancer Res. 52:5647-5655 (1992).

Herlyn et al., "Specific detection of anti-idiotypic immune responses in cancer patients treated with murine monoclonal antibody", J. Immunol. Methods 85:27-38 (1985).

Herlyn et al., "Anti-idiotype immunization of cancer patients: Modulation of the immune response", Proc. Natl. Acad. Sci. USA 84:8055-8059 (1987).

Ikeda et al., "Epitope mapping of the carcinoembryonic antigen with various related recombinant proteins expressed in chinese hamster ovary cells and 25 distinct monoclonal antibodies", Mol. Immunol. 29(2):229-240 (1992).

Ioannides et al., "T cell recognition of human tumors: implications for molecular immunotherapy of cancer", Clin. Immunol. Immunopath. 66:91-106 (Feb. 1993).

Irvine et al., "Comparison of CEA-Recombinant Vaccinia Virus, Purified CEA, and an Anti-Idiotype Antibody Bearing the Image of a CEA Epitope in the Treatment and Prevention of CEA-Expressing Tumors", Vaccine Res. 2(2):79-94 (1993).

Kennedy et al., "Antibody to Hepatitis B Virus Induced by Injecting Antibodies to the Idiotype", Science 223:930-931 (1984).

Kos et al., "Requirement for Natural Killer Cells in the Induction of Cytotoxic T Cells", J. Immunol. 155:578-584 (1995).

Kresina et al., "Antiidiotypic Antibody Vaccine in Murine *Schistosomiasis mansoni* Comprising the Internal Image of Antigen", J. Clin. Invest. 83:912-920 (1989).

Lanzavecchia et al., "The use of hybrid hybridomas to target human cytotoxic T lymphocytes", Eur. J. Immun. 17:105-111 (1987).

Losman et al., "Baboon anti-idiotype antibodies mimic a carcinoembryonic antigen epitope", Int. J. Cancer 46:310-314 (1990).

Losman et al., "Human response against NP-4, a mouse antibody to carcinoembryonic antigen: Human anti-idiotype antibodies mimic an epitope on the tumor antigen", Proc. Natl. Acad. Sci. USA 88:3421-3425 (Apr. 1991).

Losman et al., "Mimicry of a carcinoembryonic antigen epitope by a rat monoclonal anti-idiotype antibody", Int. J. Cancer 56:580-584 (1994).

Machy et al., "Endocytosis and recycling of MHC-encoded class II molecules by mouse B lymphocytes", J. Immunol. 145(5):1350-1355 (1990).

McNamara et al., "Monoclonal Idiotype Vaccine Against *Streptococcus pneumoniae* Infection", Science 226:1325-1326 (1984).

Mittelman et al., "Kinetics of the immune response and regression of metastatic lesions following development of humoral anti-high molecular weight-melanoma associated antigen immunity in three patients with advanced malignant melanoma immunized with mouse antiidiotypic monoclonal antibody MK2-23", Cancer Res. 54:415-421(1994).

Moldenhauer et al., "Surface-expressed invariant chain (CD74) is required for internalization of human leucocyte antigen-DR molecules to early endosomal compartments", Immunol. 96:473-484 (1999).

Monestier et al., "Syngeneic Anti-idotype Monoclonal Antibodies to Murine Anticarcinoembryonic Antigen Monoclonal Antibodies", Cancer Res. 49:123-126 (1989).

Morton et al., Delivery of Nascent MHC Class II-Invariant Chain Complexes to Lysosomal Compartments and Proteolysis of Invariant Chain by Cysteine Proteases Preceded Peptide Binding in B-Lymphoblastoid Cells, J. Immunol. 154:137-150 (1995).

Nepom et al., "Induction of immunity to a human tumor marker by in vivo administration of anti-idiotypic antibodies in mice", Proc. Natl. Acad. Sci. USA 81:2864-2867 (1984).

Nohria et al., "Cytokines as potential vaccine adjuvants", Biotherapy 7:261-269 (1994).

Pathak et al., "Endocytic Recycling is Required for the Presentation of an Exogenous Peptide via MHC Class II Molecules", Traffic 1:561-569 (2000).

Paul, W., (ed.), Fundamental Immunology, 3rd Ed., Raven Press, New York, 1993, p. 242.

Pawlak-Byczkowska et al. "Two New Monoclonal Antibodies, EPB-1 and EPB-2, Reactive with Human Lymphoma", Cancer Res. 49:4568-4577 (1989).

Powell et al., "Induction of effective immunity to moloney murine sarcoma virus using monoclonal anti-idiotypic antibody as immunogen", J. Immunol. 142(4):1318-1324 (1989).

Primus et al., "Immunological Heterogeneity of Carcinoembryonic Antigen: Antigenic Determinants on Carcinoembryonic Antigen Distinguished by Monoclonal Antibodies", Cancer Res. 43:686-692 (1983).

Pupa et al., "Activation of mononuclear cells to be used for hybrid monoclonal antibody-induced lysis of human ovarian carcinoma cells", Int. J. Cancer 42:455-459 (1988).

Renner et al., "Cure of xenografted human tumors by bispecific monoclonal antibodies and human T cells", Science 264:833-835 (1994).

Roche et al., "Cell surface HLA-DR-invariant chain complexes are targeted to endosomes by rapid internalization", Proc. Natl. Acad. Sci. USA 90:8581-8585 (1993).

Altomonte et al., "Targeting of HLA-DR molecules transduces agonistic functional signals in cutaneous melanoma", J Cell Physiol. 2004;200:272-276.

Aoudjit et al., "HLA-DR signaling inhibits Fas-mediated apoptosis in A375 melanoma cells", Exp Cell Res. 2004;299:79-90.

Blancheteau et al., "HLA class II signals sensitize B lymphocytes to apoptosis via Fas/CD95 by increasing FADD recruitment to activated Fas and activation of caspases", Hum Immunol. 2002;63:375-383.

Bridges et al., "Selective in vivo antitumor effects of monoclonal anti-I-A antibody on a B lymphoma", J Immunol. 1987;139:4242-4249.

Brozek et al., "Anti-DR antibodies inhibit in vitro production of human rheumatoid factor", J Clin Lab Immunol. 1990;31:105-109.

Elsasser et al., "HLA class II as potential target antigen on malignant B cells for therapy with bispecific antibodies in combination with granulocyte colony-stimulating factor", Blood 1996;87:3803-3812.

Fu et al., "HLA-DR alpha chain residues located on the outer loops are involved in non-polymorphic and polymorphic antibody-binding epitopes", Hum Immunol. 1994; 39:253-260.

Gussow et al., "Humanization of monoclonal antibodies", Method Enzymol. 203:99-121, (1991).

Kabelitz et al., "Growth inhibition of Epstein-Barr virus-transformed B cells by anti-HLA-DR antibody L243: possible relationship to L243-induced down-regulation of CD23 antigen expression", Cell Immunol. 1989;120:21-30.

Lampson et al., "Two populations of Ia-like molecules on a human B cell line", J. Immunol. (1980) 125:293-299.

Lund et al., "Expression and characterization of truncated forms of humanized L243 IgG1. Architectural features can influence synthesis of its oligosaccharide chains and affect superoxide production triggered through human Fcgamma receptor I", Eur. J. Biochem. Dec. 2000. vol. 267, No. 24, pp. 7246-7257.

Nagy et al., "Fully human, HLA-DR-specific monoclonal antibodies efficiently induce programmed death of malignant lymphoid cells", Nat Med. 2002;8:801-807.

Roitt et al., Immunology, 3rd Ed., Mosby, London, 1993, p. 6.9.

Rosenthal et al., "Human tumor vaccines and genetic engineering of tumors with cytokine and histocompatibility genes to enhance immunogenicity", Curr. Opin. Oncol. 6:611-615 (1994).

Shan et al., "Constitutive Endocytosis and Degradation of CD22 by Human B Cells", J. Immunol. 154:4466-4475 (1995).

Stein et al., "Neonatal administration of idiotype or antiidiotype primes for protection against *Escherichia coli* K13 infection in mice", J. Exp. Med. 160(4):1001-11 (1984).

Stein et al., "HLA-DR as a target for therapy of human and canine B-cell malignancies", Proc. Amer. Assoc. Cancer Res. 2009, 50:301, Abstr #1255.

Tedder et al., "Cloning of a complementary DNA encoding a new mouse B lymphocyte differentiation antigen, homologous to the human B1 (CD20) antigen, and localization of the gene to chromosome 19", J. Immunol. 141 (12):4388-94 (1988).

Traub et al., "Antiidiotype Antibodies in Cancer Patients Receiving Monoclonal Antibody to Carcinoembryonic Antigen", Cancer Res. 48:4002-4006 (1988).

Tsang et al., "A Recombinant CEA-Vaccinia Vaccine Induces a CEA-Specific Cytotoxic T-cell Response in Carcinoma Patients", Proc. Amer. Assoc. Cancer Res. vol. 36, p. 249, Abstract #1483 (1995).

Van Dijk et al., "Induction of tumor-cell lysis by bi-specific monoclonal antibodies recognizing renal-cell carcinoma and CD3 antigen", Int. J. Cancer 43:344-349 (1989).

Van Duk et al., "Bispecific antibodies reactive with the multidrug-resistance-related glycoprotein and CD3 induce lysis of multidrug-resistant tumor cells", Int. J. Cancer 44:738-743 (1989).

Van Kaer, L., "Accessory Proteins that Control the Assembly of MHC Molecules with Peptides", Immunologic Res. 23-2/3:205-214 (2001).

Vaswani et al., "Humanized antibodies as potential therapeutic drugs", Ann. Allergy Asthma Immunol. 1998; 81:105-119.

Waldmann et al., "Monoclonal Antibodies in Diagnosis and Therapy", Science 252:1657-1662 (1991).

Xu et al., "The Novelty of Antigen-Processing Compartments", J. Immunol. 155(4):1652-4 (1995).

Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56:244-248 (1994).

* cited by examiner

*Primary Examiner* — Phuong Huynh

(74) *Attorney, Agent, or Firm* — Richard A. Nakashima

(57) ABSTRACT

The present invention relates to methods and compositions for pretargeting delivery of therapeutic agents. In preferred embodiments, the pretargeting method comprises: a) administering a bispecific antibody with a first binding site for a disease-associated antigen and a hapten on a targetable construct; b) administering a targetable construct comprising at least one therapeutic agent. In preferred embodiments, the bispecific antibody is made by the dock-and-lock (DNL) technique. In a more preferred embodiment, the targetable construct comprises one or more SN-38 moieties.

10 Claims, 4 Drawing Sheets

SEQUENCE LISTING

```
<160> NUMBER OF SEQ ID NOS: 83

<210> SEQ ID NO 1
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1
aatgcggcgg tggtgacagt a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagctcagca cacagaaaga c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uaaaaucuuc cugcccacct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ggaagcuguu ggcugaaaat t                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aagaccagcc ucuuugccca g                                              21

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggaccaggca gaaaacgag                                                 19
```

```
<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuaucaggau gacgcgg                                                    17

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugacacaggc aggcuugacu u                                               21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggtgaagaag ggcgtccaa                                                  19

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatccgttgg agctgttggc gtagttcaag agactcgcca acagctccaa cttttggaaa    60

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aggtggtgtt aacagcagag                                                 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaggtggagc aagcggtgga g                                               21

<210> SEQ ID NO 13
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaggagttga aggccgacaa a                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uauggagcug cagaggaugt t                                              21

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttgaatatc tgtgctgaga acacagttct cagcacagat attcttttt               49

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatgagaaaa gcaaaaggtg ccctgtctc                                      29

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaucaucauc aagaaagggc a                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
augacuguca ggauguugct t                                              21
```

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaacgaaucc ugaagacauc u                                              21

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagcctggct acagcaatat gcctgtctc                                      29

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ugaccaucac cgaguuuaut t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagtcggacg caacagagaa a                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
cuaccuuucu acggacgugt t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgcctaagg cggatttgaa t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ttauuccuuc uucgggaagu c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaccttctgg aacccgccca c                                              21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagcatcttc gagcaagaa                                                 19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
catgtggcac cgtttgcct                                                 19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aactaccaga aaggtatacc t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic

```
    oligonucleotide
<220> FEATURE:
<223> OTHER INFORMATION: Description of Combined DNA/RNA Molecule:
      Synthetic oligonucleotide

<400> SEQUENCE: 30
ucacaguguc cuuuauguat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
gcaugaaccg gaggcccaut t                                              21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccggacagtt ccatgtata                                                 19

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser His Ile Gln Ile Pro Pro Gly Leu Thr Glu Leu Leu Gln Gly Tyr
1               5                   10                  15
Thr Val Glu Val Leu Arg Gln Gln Pro Pro Asp Leu Val Glu Phe Ala
            20                  25                  30
Val Glu Tyr Phe Thr Arg Leu Arg Glu Ala Arg Ala
        35                  40

<210> SEQ ID NO 34
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Cys Gly His Ile Gln Ile Pro Pro Gly Leu Thr Glu Leu Leu Gln Gly
1               5                   10                  15
Tyr Thr Val Glu Val Leu Arg Gln Gln Pro Pro Asp Leu Val Glu Phe
            20                  25                  30
Ala Val Glu Tyr Phe Thr Arg Leu Arg Glu Ala Arg Ala
        35                  40                  45

<210> SEQ ID NO 35
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Glu Tyr Leu Ala Lys Gln Ile Val Asp Asn Ala Ile Gln Gln
1               5                   10                  15

Ala

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 37
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 38
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 39
<211> LENGTH: 23
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 40
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 42
<211> LENGTH: 51
<212> TYPE: PRT
<213> ORGANISM: Homo sapiens

<400> SEQUENCE: 42

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 43
<211> LENGTH: 54
<212> TYPE: PRT
<213> ORGANISM: Homo sapiens
```

```
-continued

<400> SEQUENCE: 43

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Lys Glu Glu
        35                  40                  45

Asn Arg Gln Ile Leu Ala
        50

<210> SEQ ID NO 44
<211> LENGTH: 44
<212> TYPE: PRT
<213> ORGANISM: Homo sapiens

<400> SEQUENCE: 44

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 45
<211> LENGTH: 44
<212> TYPE: PRT
<213> ORGANISM: Homo sapiens

<400> SEQUENCE: 45

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Val Ala Lys Gln Ile Val Asp Tyr Ala Ile His Gln
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Lys Ala Lys Gln Ile Val Asp His Ala Ile His Gln
1               5                   10                  15

Ala
```

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr His Ala Lys Gln Ile Val Asp His Ala Ile His Gln
1               5                   10                  15

Ala

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Val Ala Lys Gln Ile Val Asp His Ala Ile His Gln
1               5                   10                  15

Ala

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Leu Glu Tyr Gln Ala Gly Leu Leu Val Gln Asn Ala Ile Gln Gln
1               5                   10                  15

Ala Ile

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Leu Ile Glu Thr Ala Ser Ser Leu Val Lys Asn Ala Ile Gln Leu
1               5                   10                  15

Ser Ile

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Ile Glu Glu Ala Ala Ser Arg Ile Val Asp Ala Val Ile Glu Gln
1               5                   10                  15

Val Lys
```

```
<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Leu Tyr Gln Phe Ala Asp Arg Phe Ser Glu Leu Val Ile Ser Glu
1               5                   10                  15

Ala Leu

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Glu Gln Val Ala Asn Gln Leu Ala Asp Gln Ile Ile Lys Glu Ala
1               5                   10                  15

Thr

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Glu Glu Leu Ala Trp Lys Ile Ala Lys Met Ile Trp Ser Asp Val
1               5                   10                  15

Phe

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Leu Val Arg Leu Ser Lys Arg Leu Val Glu Asn Ala Val Leu Lys
1               5                   10                  15

Ala Val

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ala Glu Glu Val Ser Ala Arg Ile Val Gln Val Val Thr Ala Glu
1               5                   10                  15

Ala Val
```

-continued

```
<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ile Lys Gln Ala Ala Phe Gln Leu Ile Ser Gln Val Ile Leu Glu
1               5                   10                  15

Ala Thr

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ala Trp Lys Ile Ala Lys Met Ile Val Ser Asp Val Met Gln Gln
1               5                   10                  15

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Glu Gln Tyr Ala Asn Gln Leu Ala Asp Gln Ile Ile Lys Glu Ala
1               5                   10                  15

Thr Glu

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Glu Glu Leu Ala Trp Lys Ile Ala Lys Met Ile Trp Ser Asp Val
1               5                   10                  15

Phe Gln Gln Cys
            20
```

```
<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ile Glu Tyr Leu Ala Lys Gln Ile Pro Asp Asn Ala Ile Gln Gln
1               5                   10                  15

Ala

<210> SEQ ID NO 64
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 65
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 66
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Glu Asp Ala Glu Leu Val Arg Thr Ser Lys Arg Leu Val Glu Asn
1               5                   10                  15
```

Ala Val Leu Lys Ala Val Gln Gln Tyr
            20                  25

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 72

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 77
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
```

```
<221> NAME/KEY: MOD_RES
<222> LOCATION: (4)..(4)
<223> OTHER INFORMATION: Lys(HSG)
<220> FEATURE:
<223> OTHER INFORMATION: C-term amidated

<400> SEQUENCE: 81

Phe Lys Tyr Lys
1

<210> SEQ ID NO 82

<400> SEQUENCE: 82

000

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Gly Gln Ile Glu Tyr Leu Ala Lys Gln Ile Val Asp Asn Ala Ile
1               5                   10                  15

Gln Gln Ala Gly Cys
            20
```

US 8,435,539 B2

DELIVERY SYSTEM FOR CYTOTOXIC DRUGS BY BISPECIFIC ANTIBODY PRETARGETING

RELATED APPLICATIONS

This application is a continuation-in-part of U.S. patent application Ser. Nos. 12/949,536, filed Nov. 18, 2010, (which was a divisional of Ser. No. 12/396,605, filed Mar. 3, 2009, which was a divisional of Ser. No. 11/633,729, filed Dec. 5, 2006, now U.S. Pat. No. 7,527,787); 12/915,515, filed Oct. 29, 2010; 12/871,345, filed Aug. 30, 2010; 12/869,823, filed Aug. 27, 2010; 12/754,740, filed Apr. 6, 2010; 12/752,649, filed Apr. 1, 2010; 12/731,781, filed Mar. 25, 2010; 12/644,146 (which was a divisional of Ser. No. 11/925,408, filed Oct. 26, 2007, now U.S. Pat. No. 7,666,400), filed Dec. 22, 2009; 12/544,476, filed Aug. 20, 2009; 12/468,589 (which was a divisional of Ser. No. 11/389,358, filed Mar. 24, 2006, now U.S. Pat. No. 7,550,143), filed May 19, 2009; 12/418,877, filed Apr. 6, 2009; 12/417,917 (which was a divisional of Ser. No. 11/478,021, filed Jun. 29, 2006, now U.S. Pat. No. 7,534,866), filed Apr. 3, 2009; and 12/396,965 (which was a divisional of Ser. No. 11/391,584, filed Mar. 28, 2006, now U.S. Pat. No. 7,521,056), filed Mar. 3, 2009. Those applications claimed the benefit under 35 U.S.C. 119(e) of provisional U.S. Patent Applications 61/378,059, filed Aug. 30, 2010; 61/323,960, filed Apr. 14, 2010; 61/316,996, filed Mar. 24, 2010; 61/266,305, filed Dec. 3, 2009; 61/258,729, filed Nov. 6, 2009; 61/258,369, filed Nov. 5, 2009; 61/238,424, filed Aug. 31, 2009; 61/238,473, filed Aug. 31, 2009; 61/168,715, filed Apr. 13, 2009; 61/168,668, filed Apr. 13, 2009; 61/168,657, filed Apr. 13, 2009; 61/168,290, filed Apr. 10, 2009; 61/166,809, filed Apr. 6, 2009; 61/163,666, filed Mar. 26, 2009; 61/119,542, filed Dec. 3, 2008; 61/104,916, filed Oct. 13, 2008; 61/090,487, filed Aug. 20, 2008; 61/043,932, filed Apr. 10, 2008; 60/864,530, filed Nov. 6, 2006; 60/782,332, filed Mar. 14, 2006; 60/751,196, filed Dec. 16, 2005; 60/728,292, filed Oct. 19, 2005; 60/668,603, filed Apr. 6, 2005; and 60/544,227, filed Feb. 13, 2004.

This application claims the benefit of U.S. Provisional Patent Application 61/267,998, filed Dec. 9, 2009. The text of each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 27, 2010, is named IMM325US.txt and is 29,077 bytes in size.

FIELD OF THE INVENTION

The present invention relates to therapeutic conjugates with improved ability to target diseases, such as cancer, infectious disease, autoimmune disease, immune dysfunction (e.g., graft versus host disease, organ transplant rejection), cardiovascular disease, metabolic disease and neurologic (e.g., neurodegenerative) disease. Preferably, the delivery system comprises a pretargeting method in which bispecific antibodies have one or more binding sites for a disease associated antigen and one or more binding sites for a hapten on a targetable construct. The targetable construct may comprise therapeutic agents, such as cytotoxic drugs, and/or diagnostic agents, such as radionuclides. More preferably, the cytotoxic drug may be SN-38. Most preferably, the bispecific antibody is made by the dock-and-lock (DNL) technique.

BACKGROUND OF THE INVENTION

Monoclonal antibodies have been used for the targeted delivery of toxic agents to cancer and other diseased cells. However, immunoconjugates of antibodies and toxic agents have had mixed success in the therapy of cancer or autoimmune disease, and little application in other diseases, such as infectious disease. The toxic agent is most commonly a chemotherapy drug, although particle-emitting radionuclides, or bacterial or plant toxins have also been conjugated to antibodies, especially for the therapy of cancer (Sharkey and Goldenberg, 2006, CA Cancer J Clin 56:226-243) and with radioimmunoconjugates for the preclinical therapy of certain infectious diseases (Dadachova and Casadevall, 2006, Q J Nucl Med Mol Imaging 50:193-204).

Camptothecin (CPT) and its derivatives are a class of potent antitumor agents. Irinotecan (also referred to as CPT-11) and topotecan are CPT analogs that are approved cancer therapeutics (Iyer and Ratain, 1998, Cancer Chemother Phamacol 42:S31-S43). CPTs act by inhibiting topoisomerase I (Hsiang et al., 1985, J Biol Chem 260:14873-78). Although potent cytotoxic agents, therapeutic use of camptothecins is limited by its relative insolubility in aqueous solution and high systemic toxicity, which limits the effective dosage that may be delivered to targeted disease cells. A need exists in the field for more effective targeted delivery methods for camptothecins and other therapeutic agents.

SUMMARY OF THE INVENTION

The present invention resolves an unfulfilled need in the art by providing improved methods and compositions for targeted delivery of therapeutic agents. In preferred embodiments, the methods and compositions comprise pretargeting with novel bispecific antibody constructs, which contain at least one binding site for a disease associated antigen, such as a tumor-associated antigen, a B-cell associated antigen, or a pathogen-associated antigen, and at least one binding site for a hapten on a targetable construct. The targetable construct serves as a carrier for therapeutic or diagnostic agents.

More preferably, the bispecific antibody constructs are prepared by the dock-and-lock (DNL) technique (see, e.g., U.S. Pat. Nos. 7,550,143; 7,521,056; 7,534,866; 7,527,787 and 7,666,400, the Examples section of each incorporated herein by reference). The DNL technique utilizes the specific binding interactions occurring between a dimerization and docking domain (DDD moiety) from protein kinase A, and an anchoring domain (AD moiety) from any of a number of known A-kinase anchoring proteins (AKAPs). The DDD moieties spontaneously form dimers which then bind to an AD moiety. By attaching appropriate effector moieties, such as antibodies or fragments thereof, to AD and DDD moieties, the DNL technique allows the specific covalent formation of any desired targeted delivery complex. Where the effector moiety is a protein or peptide, the AD and DDD moieties may be incorporated into fusion proteins conjugated to the effector moieties.

Antibodies or other targeting molecules of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1α, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

Exemplary antibodies that may be utilized include, but are not limited to, hR1 (anti-IGF-1R, U.S. patent application Ser. No. 12/722,645, filed Mar. 12, 2010), hPAM4 (anti-mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

An antibody or antigen-binding fragment of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. As discussed below, techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As also discussed below, techniques for production of human antibodies are also well known.

Various embodiments may concern use of the subject methods and compositions to treat a disease, including but not limited to non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas, melanomas, sarcomas, gliomas, and skin cancers. The carcinomas may be selected from the group consisting of carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes.

In addition, the subject methods and compositions may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

In certain embodiments, disease therapy may be enhanced by combination therapy with one or more other therapeutic agents. Known therapeutic agents of use include toxins, immunomodulators (such as cytokines, lymphokines, chemokines, growth factors and tumor necrosis factors), hormones, hormone antagonists, enzymes, oligonucleotides (such as siRNA or RNAi), photoactive therapeutic agents, anti-angiogenic agents and pro-apoptotic agents. The therapeutic agents may be delivered by conjugation to the same or different antibodies or other targeting molecules or may be administered in unconjugated form. Other therapeutic agents may be administered before, concurrently with or after the bispecific antibody and targetable construct.

In a preferred embodiment, the therapeutic agent is a cytotoxic agent, such as a drug or a toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzyme inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, SN-38, doxorubicins and their analogs, antimetabolites, alkylating agents, antimitotics, anti-angiogenic agents, tyrosine kinase inhibitors, mTOR inhibitors, heat shock protein (HSP90) inhibitors, proteosome inhibitors, HDAC inhibitors, pro-apoptotic agents, methotrexate, CPT-11, and a combination thereof.

In another preferred embodiment, the therapeutic agent is a toxin selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin and combinations thereof. Or an immunomodulator selected from the group consisting of a cytokine, a stem cell growth factor, a lymphotoxin, a hematopoietic factor, a colony stimulating factor (CSF), an interferon (IFN), erythropoietin, thrombopoietin and a combinations thereof.

In other preferred embodiments, the therapeutic agent is a radionuclide selected from the group consisting of $^{111}$In, $^{177}$Lu, $^{212}$B, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. In other embodiments the therapeutic agent is a photoactive therapeutic agent selected from the group consisting of chromogens and dyes.

Alternatively, the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

The disclosed methods and compositions may thus be applied for treatment of diseases and conditions for which targeting moieties are of use to deliver cytotoxic agents. Such diseases or conditions may be characterized by the presence of a target molecule or target cell that is insufficiently affected when unconjugated, or naked, targeting moieties are used, such as in the immunotherapy of cancer or of infection with pathogenic organisms. (For methods of making immunoconjugates of antibodies with isotopes, drugs, and toxins for use in disease therapies, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; 7,259,240 and U.S. Patent Appln. Publ. Nos. 20050175582 (now abandoned); 20050136001; 20040166115 (now abandoned); 20040043030 (now abandoned); 20030068322 (now abandoned) and 20030026764 (now abandoned), the Examples section of each incorporated herein by reference.)

Camptothecin (CPT) and its analogs and derivatives are preferred chemotherapeutic moieties, although the invention is not so limited. Other chemotherapeutic moieties that are within the scope of the invention are taxanes (e.g, baccatin III, taxol), calicheamicin, epothilones, anthracycline drugs (e.g., doxorubicin (DOX), epirubicin, morpholinodoxorubicin (morpholino-DOX), cyanomorpholino-doxorubicin (cyano-morpholino-DOX), and 2-pyrrolinodoxorubicin (2-PDOX); see Priebe W (ed.), ACS symposium series 574, published by American Chemical Society, Washington D.C., 1995 (332 pp) and Nagy et al., *Proc. Natl. Acad. Sci. USA* 93:2464-2469, 1996), benzoquinoid ansamycins exemplified by geldanamycin (DeBoer et al., *Journal of Antibiotics* 23:442-447, 1970; Neckers et al., *Invest. New Drugs* 17:361-373, 1999), and the like.

In certain embodiments involving treatment of cancer, the drug conjugates may be used in combination with surgery, radiation therapy, chemotherapy, immunotherapy with naked antibodies, radioimmunotherapy, immunomodulators, vaccines, and the like. Similar combinations are preferred in the treatment of other diseases amenable to targeting moieties, such as autoimmune diseases. For example, camptothecin conjugates can be combined with TNF inhibitors, B-cell antibodies, interferons, interleukins, and other effective agents for the treatment of autoimmune diseases, such as rheumatoid arthritis, systemic lupus erythematosis, Sjögren's syndrome, multiple sclerosis, vasculitis, as well as type-I diabetes (juvenile diabetes). These combination therapies can allow lower doses of each therapeutic to be given in such combinations, thus reducing certain severe side effects, and potentially reducing the courses of therapy required. In viral diseases, the drug conjugates can be combined with other therapeutic drugs, immunomodulators, naked antibodies, or vaccines (e.g., antibodies against hepatitis, HIV, or papilloma viruses, or vaccines based on immunogens of these viruses). Antibodies and antigen-based vaccines against these and other viral pathogens are known in the art and, in some cases, already in commercial use.

DETAILED DESCRIPTION OF THE INVENTION

Definitions

Figure 1:
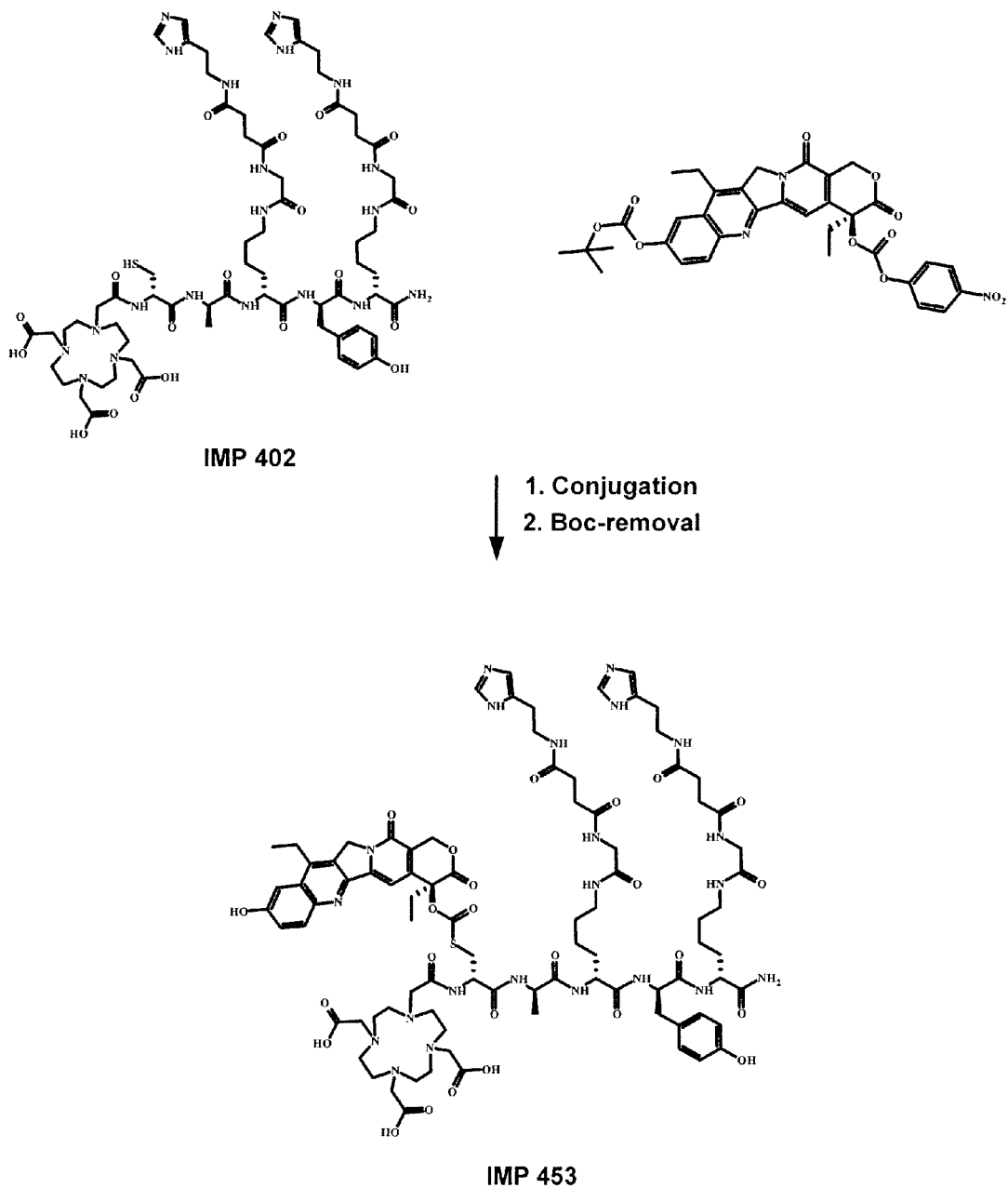
FIG. 1. Synthesis of IMP 453.

Unless otherwise specified, "a" or "an" means one or more.
As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, Fab', Fab, Fv, sFv and the like. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B-cell. Phage display can be performed in a variety of formats, for review, see e.g. Johnson and Chiswell, Current Opinion in Structural Biology 3:5564-571 (1993). Human antibodies may also be generated by in vitro activated B-cells. See U.S. Pat. Nos. 5,567,610 and 5,229,275, the Examples section of which is incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

CPT is abbreviation for camptothecin, and as used in the present application CPT represents camptothecin itself or an analog or derivative of camptothecin. The structures of camptothecin and some of its analogs, with the numbering indicated and the rings labeled with letters A-E, are shown below.

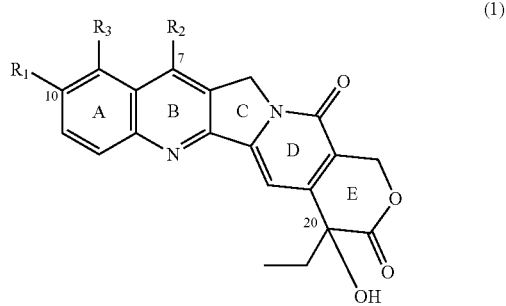

(1)

CPT: $R_1=R_2=R_3=H$
10-Hydroxy-CPT: $R_1=OH; R_2=R_3=H$
CPT-11:

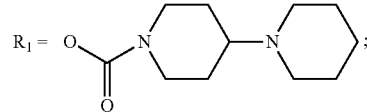

$R_2$=ethyl; $R_3$=H
SN-38: $R_1=OH; R_2$=ethyl; $R_3=H$
Topotecan: $R_1=OH; R_2=H; R_3=CH_2-N(CH_3)_2$ In a preferred embodiment, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In a more preferred embodiment, the chemotherapeutic moiety is SN-38.

Targetable Constructs

In certain embodiments, the moiety labeled with one or more diagnostic and/or therapeutic agents may comprise a peptide or other targetable construct. Labeled peptides (or proteins) may be selected to bind directly to a targeted cell, tissue, pathogenic organism or other target. In other embodiments, labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies or multi-specific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO:81), wherein DOTA is 1,4,7,10-tetraazacyclododecane1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid), DTPA or other known chelating moieties.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

In alternative embodiments, the specificity of the click chemistry reaction may be used as a substitute for the antibody-hapten binding interaction used in pretargeting with bispecific antibodies. As discussed below, the specific reactivity of e.g., cyclooctyne moieties for azide moieties or alkyne moieties for nitrone moieties may be used in an in vivo cycloaddition reaction. An antibody or other targeting molecule is activated by incorporation of a substituted cyclooctyne, an azide or a nitrone moiety. A targetable construct is labeled with one or more diagnostic or therapeutic agents and a complementary reactive moiety. I.e., where the targeting molecule comprises a cyclooctyne, the targetable construct will comprise an azide; where the targeting molecule comprises a nitrone, the targetable construct will comprise an alkyne, etc. The activated targeting molecule is administered to a subject and allowed to localize to a targeted cell, tissue or pathogen, as disclosed for pretargeting protocols. The reactive labeled targetable construct is then administered. Because the cyclooctyne, nitrone or azide on the targetable construct is unreactive with endogenous biomolecules and highly reactive with the complementary moiety on the targeting molecule, the specificity of the binding interaction results in the highly specific binding of the targetable construct to the tissue-localized targeting molecule.

The skilled artisan will realize that although the majority of targetable constructs disclosed in the Examples below are peptides, other types of molecules may be used as targetable constructs. For example, polymeric molecules, such as polyethylene glycol (PEG), may be easily derivatized with functional groups to bind diagnostic or therapeutic agents. Following attachment of an appropriate reactive group, such as a substituted cyclooctyne, a nitrone or an azide, the labeled polymer may be utilized for delivery of diagnostic or therapeutic agents. Many examples of such carrier molecules are known in the art and may be utilized, including but not limited to polymers, nanoparticles, microspheres, liposomes and micelles.

Antibodies

Target Antigens

Targeting antibodies of use may be specific to or selective for a variety of cell surface or disease-associated antigens. Exemplary target antigens of use for imaging or treating various diseases, conditions, syndromes or disorders, such as a malignant disease, a cardiovascular disease, an infectious disease, an inflammatory disease, an autoimmune disease, a metabolic (e.g., endocrine) disease, or a neurological (e.g., neurodegenerative) disease, such as Alzheimer's, may include carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1a, AFP, PSMA, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, C5, PLAGL2, and an oncogene product.

In certain embodiments, such as treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Reports on tumor associated antigens (TAAs) include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACT). See Yu et al. Nat. Immunol. 1:252-256 (2000). Briefly, TACI is a marker for B-cell malignancies (e.g., lymphoma). TACI and B-cell maturation antigen (BCMA) are bound by the tumor necrosis factor homolog—a proliferation-inducing ligand (APRIL). APRIL stimulates in vitro proliferation of primary B and T-cells and increases spleen weight due to accumulation of B-cells in vivo. APRIL also competes with TALL-I (also called BLyS or BAFF) for receptor binding. Soluble BCMA and TACI specifically prevent binding of APRIL and block APRIL-stimulated proliferation of primary B-cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T-cell function.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, CXCR4, B7, MUC1, Ia, Ii, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

Methods for Raising Antibodies

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, Genet. Mol. Res. 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the t, y and x chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies

The skilled artisan will realize that the targeting molecules of use may incorporate any antibody or fragment known in the art that has binding specificity for a target antigen associated with a disease state or condition. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662,378, U.S. patent application Ser. No. 12/846,062, filed Jul. 29, 2010), hRS7 (anti-EGP-1, U.S. Pat. No. 7,238,785) and hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agents Chemother. 2006; 50(5):1773-9, all incorporated herein by reference.

In one embodiment, a pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Anti-CD3 antibodies have been proposed for therapy of type 1 diabetes (Cemea et al., 2010, Diabetes Metab Rev 26:602-05). In addition, a pharmaceutical composition of the present invention may be used to treat a subject having an immune-dysregulatory disorder such as graft-versus-host disease or organ transplant rejection.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

Where bispecific antibodies are used, the second MAb may be selected from any anti-hapten antibody known in the art, including but not limited to h679 (U.S. Pat. No. 7,429,381) and 734 (U.S. Pat. Nos. 7,429,381; 7,563,439; 7,666,415; and 7,534,431), the Examples section of each of which is incorporated herein by reference.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.) Such known antibodies are of use for detection and/or treating a variety of disease states or conditions (e.g., hMN-14 or TF2 (CEA-expressing carcinomas), hA20 or TF-4 (lymphoma), hPAM4 or TF-10 (pancreatic cancer), RS7 (lung, breast, ovarian, prostatic cancers), hMN-15 or hMN3 (inflammation), anti-gp120 and/or anti-gp41 (HIV), anti-platelet and anti-thrombin (blood clots), anti-myosin (cardiac necrosis), anti-CXCR4 (cancer and inflammatory disease)).

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206'; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments which recognize specific epitopes can be generated by known techniques. The antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science,* 246:1274-1281) to allow rapid and easy identification of monoclonal Fab' fragments with the desired specificity. An antibody fragment can be prepared by proteolytic hydrolysis of the full length antibody or by expression in *E. coli* or another host of the DNA coding for the fragment. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single chain Fv molecule (scFv) comprises a $V_L$ domain and a $V_H$ domain. The $V_L$ and $V_H$ domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991), incorporated herein by reference.

An scFv library with a large repertoire can be constructed by isolating V-genes from non-immunized human donors using PCR primers corresponding to all known $V_H$, $V_{kappa}$ and $V_{80}$ gene families. See, e.g., Vaughn et al., Nat. Biotechnol., 14: 309-314 (1996). Following amplification, the $V_{kappa}$ and $V_{lambda}$ pools are combined to form one pool. These fragments are ligated into a phagemid vector. The scFv linker is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned for binding to the selected antigen.

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001) Alpaca serum IgG contains about 50% camelid heavy chain only IgG antibodies (Cabs) (Maass et al., 2007). Alpacas may be immunized with known antigens and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). These and other known antigen-binding antibody fragments may be utilized in the claimed methods and compositions.

General Techniques for Antibody Cloning and Production

Various techniques, such as production of chimeric or humanized antibodies, may involve procedures of antibody cloning and construction. The antigen-binding $V_K$ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The $V_K$ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for $V_K$ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the $V_K$ and $V_H$ sequences together with the promoter and signal peptide sequences can be excised from VKpBR and VHpBS and ligated into appropriate expression vectors, such as pKh and pGlg, respectively (Leung et al., Hybridoma, 13:469 (1994)). The expression vectors can be co-transfected into an appropriate cell and supernatant fluids monitored for production of a chimeric, humanized or human MAb. Alternatively, the $V_K$ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

In certain embodiments, the techniques and compositions for therapeutic agent delivery disclosed herein may be used with bispecific or multispecific antibodies as the targeting moieties. Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,550,143; 7,521,056; 7,534,866; 7,527,787 and U.S. Ser. No. 11/925,408, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens.

Dock-and-Lock (DNL)

In preferred embodiments, bispecific or multispecific antibodies or other constructs may be produced using the dock-and-lock technology (see, e.g., U.S. Pat. Nos. 7,550,143; 7,521,056; 7,534,866; 7,527,787 and 7,666,400, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RID, and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In other alternative embodiments, click chemistry reactions may be used to produce an AD or DDD peptide conjugated to an effector moiety, or even to covalently attach the AD and DDD moiety to each other to provide an irreversible covalent bond to stabilize the DNL complex.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074,405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

In preferred embodiments, a therapeutic or diagnostic agent may be covalently attached to an antibody or antibody fragment to form an immunoconjugate. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted akyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or $V_\kappa$ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above. Alternatively, methods of chemical conjugation of such moieties to biomolecules are well known in the art, and any such known method may be utilized.

Therapeutic and Diagnostic Agents

In certain embodiments, the targeting molecules or targetable constructs disclosed herein may be attached to one or more therapeutic and/or diagnostic agents. Therapeutic agent are preferably selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT.

Chemokines of use include RANTES, MCAF, MIP1-alpha, MIP1-Beta and IP-10.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photo-activated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (P1GF) peptides and antibodies, anti-vascular growth factor antibodies (such as anti-VEGF and anti-P1GF), anti-Fik-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise and oligonucleotide, such as a siRNA. The skilled artisan will realize that any siRNA or interference RNA species may be attached to a targetable construct for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bc12 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (7,781,575), and apolipoprotein B (7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 1. Although siRNA is delivered as a double-stranded molecule, for simplicity only the sense strand sequences are shown in Table 1.

TABLE 1

Exemplary siRNA Sequences

| Target | Sequence | SEQ ID NO |
|---|---|---|
| VEGF R2 | AATGCGGCGGTGGTGACAGTA | SEQ ID NO: 1 |
| VEGF R2 | AAGCTCAGCACACAGAAAGAC | SEQ ID NO: 2 |
| CXCR4 | UAAAAUCUUCCUGCCCACCdTdT | SEQ ID NO: 3 |
| CXCR4 | GGAAGCUGUUGGCUGAAAAdTdT | SEQ ID NO: 4 |
| PPARC1 | AAGACCAGCCUCUUUGCCCAG | SEQ ID NO: 5 |
| Dynamin 2 | GGACCAGGCAGAAAACGAG | SEQ ID NO: 6 |
| Catenin | CUAUCAGGAUGACGCGG | SEQ ID NO: 7 |
| E1A binding protein | UGACACAGGCAGGCUUGACUU | SEQ ID NO: 8 |
| Plasminogen activator | GGTGAAGAAGGGCGTCCAA | SEQ ID NO: 9 |
| K-ras | GATCCGTTGGAGCTGTTGGCGTAGTTCAAGAGACTCGCCAACAGCTCCAACTTTTGGAAA | SEQ ID NO: 10 |
| Sortilin 1 | AGGTGGTGTTAACAGCAGAG | SEQ ID NO: 11 |
| Apolipoprotein E | AAGGTGGAGCAAGCGGTGGAG | SEQ ID NO: 12 |
| Apolipoprotein E | AAGGAGTTGAAGGCCGACAAA | SEQ ID NO: 13 |
| Bcl-X | UAUGGAGCUGCAGAGGAUGdTdT | SEQ ID NO: 14 |
| Raf-1 | TTTGAATATCTGTGCTGAGAACACAGTTCTCAGCACAGATATTCTTTTT | SEQ ID NO: 15 |
| Heat shock transcription factor 2 | AATGAGAAAAGCAAAAGGTGCCCTGTCTC | SEQ ID NO: 16 |
| IGFBP3 | AAUCAUCAUCAAGAAAGGGCA | SEQ ID NO: 17 |
| Thioredoxin | AUGACUGUCAGGAUGUUGCdTdT | SEQ ID NO: 18 |
| CD44 | GAACGAAUCCUGAAGACAUCU | SEQ ID NO: 19 |
| MMP14 | AAGCCTGGCTACAGCAATATGCCTGTCTC | SEQ ID NO: 20 |
| MAPKAPK2 | UGACCAUCACCGAGUUUAUdTdT | SEQ ID NO: 21 |
| FGFR1 | AAGTCGGACGCAACAGAGAAA | SEQ ID NO: 22 |
| ERBB2 | CUACCUUUCUACGGACGUGdTdT | SEQ ID NO: 23 |
| BCL2L1 | CTGCCTAAGGCGGATTTGAAT | SEQ ID NO: 24 |
| ABL1 | TTAUUCCUUCUUCGGGAAGUC | SEQ ID NO: 25 |
| CEACAM1 | AACCTTCTGGAACCCGCCCAC | SEQ ID NO: 26 |
| CD9 | GAGCATCTTCGAGCAAGAA | SEQ ID NO: 27 |
| CD151 | CATGTGGCACCGTTTGCCT | SEQ ID NO: 28 |
| Caspase 8 | AACTACCAGAAAGGTATACCT | SEQ ID NO: 29 |
| BRCA1 | UCACAGUGUCCUUUAUGUAdTdT | SEQ ID NO: 30 |
| p53 | GCAUGAACCGGAGGCCCAUTT | SEQ ID NO: 31 |
| CEACAM6 | CCGGACAGTTCCATGTATA | SEQ ID NO: 32 |

The skilled artisan will realize that Table 1 represents a very small sampling of the total number of siRNA species known in the art, and that any such known siRNA may be utilized in the claimed methods and compositions.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Therapeutic Treatment

In another aspect, the invention relates to a method of treating a subject, comprising administering a therapeutically effective amount of a therapeutic conjugate as described herein to a subject. Diseases that may be treated with the therapeutic conjugates described herein include, but are not limited to B-cell malignancies (e.g., non-Hodgkin's lymphoma and chronic lymphocytic leukemia using, for example LL2 antibody; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used. Such therapeutics can be given once or repeatedly, depending on the disease state and tolerability of the conjugate, and can also be used optimally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term.

In a preferred embodiment, therapeutic conjugates comprising the Mu-9 antibody can be used to treat colorectal, as well as pancreatic and ovarian cancers as disclosed in U.S. Pat. Nos. 6,962,702 and 7,387,772, the Examples section of each incorporated herein by reference. In addition, therapeutic conjugates comprising the PAM4 antibody can be used to treat pancreatic cancer, as disclosed in U.S. Pat. Nos. 7,238,786 and 7,282,567, the Examples section of each incorporated herein by reference.

In another preferred embodiment, therapeutic conjugates comprising the RS7 antibody (binding to epithelial glycoprotein-1 [EGP-1] antigen) can be used to treat carcinomas such as carcinomas of the lung, stomach, urinary bladder, breast, ovary, uterus, and prostate, as disclosed in U.S. Pat. No. 7,238,785, the Examples section of which is incorporated herein by reference.

In another preferred embodiment, therapeutic conjugates comprising the anti-AFP antibody can be used to treat hepatocellular carcinoma, germ cell tumors, and other AFP-producing tumors using humanized, chimeric and human antibody forms, as disclosed in U.S. Pat. No. 7,300,655, the Examples section of which is incorporated herein by reference.

In another preferred embodiment, therapeutic conjugates comprising anti-tenascin antibodies can be used to treat hematopoietic and solid tumors and conjugates comprising antibodies to tenascin can be used to treat solid tumors, preferably brain cancers like glioblastomas.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz, cited above. In a preferred embodiment, the pathogens are selected from the group consisting of HIV virus, *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus, Cryptococcus neoformans, Histoplasma capsulatum, Hemophilus influenzae B. Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M arginini, Acholeplasma laidlawii, M salivarium* and *M. pneumoniae*, as disclosed in U.S. Pat. No. 6,440,416, the Examples section of which is incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 antibody (anti HIV antibody) and a toxin, such as *Pseudomonas* exotoxin, have been examined for antiviral properties (Van Oigen et al., *J Drug Target*, 5:75-91, 1998). Attempts at treating HIV infection in AIDS patients failed, possibly due to insufficient efficacy or unacceptable host toxicity. The drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agens Chemother. 2006; 50(5): 1773-9, all incorporated herein by reference. A preferred targeting agent for HIV is various combinations of these antibodies in order to overcome resistance.

In another preferred embodiment, diseases that may be treated using the therapeutic conjugates of the preferred embodiments of the present invention include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, and also juvenile diabetes, as disclosed in U.S. Provisional Application Ser. No. 60/360,259, filed Mar. 1, 2002 (now expired). Typical antibodies useful in these diseases include, but are not limited to, those reactive with HLA-DR antigens, B-cell and plasma-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, and HLA-DR), IL-6, IL-17. Since many of these autoimmune diseases are affected by autoantibodies made by aberrant B-cell populations, depletion of these B-cells by therapeutic conjugates involving such antibodies-therapeutic agent conjugates described herein is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody). In a preferred embodiment, the anti-B-cell, anti-T-cell, or anti-macrophage or other such antibodies of use in the treatment of patients with autoimmune diseases also can be conjugated to result in more effective therapeutics to control the host responses involved in said autoimmune diseases, and can be given alone or in combination with other therapeutic agents, such as TNF inhibitors or TNF antibodies, unconjugated B- or T-cell antibodies, and the like.

In a preferred embodiment, a more effective incorporation into cells and pathogens can be accomplished by using multivalent, multispecific or multivalent, monospecific antibodies. Examples of such bivalent and bispecific antibodies are found in U.S. Pat. Nos. 7,387,772; 7,300,655; 7,238,785; and 7,282,567, the Examples section of each of which is incorporated herein by reference. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

Methods of Administration

The subject molecules labeled with diagnostic or therapeutic agents may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection. Injection may be intravenous, intraarterial, intralymphatic, intrathecal, or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, it is desirable to provide the recipient with a dosage of bispecific antibody that is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject are 1 to 200 mg, more preferably 1 to 70 mg, most preferably 1 to 20 mg, although higher or lower doses may be used. Dosages of therapeutic bispecific antibodies may be higher, such as 1 to 200, 1 to 100, 100 to 1000, 100 to 500, 200 to 750 mg or any range in between.

In general, the dosage of labeled molecule(s) to administer will vary depending upon such factors as the patient's age, weight, height, sex, general medical condition and previous medical history. Preferably, a saturating dose of the labeled molecules is administered to a patient. For administration of radiolabeled molecules, the dosage may be measured by millicuries.

In preferred embodiments, the labeled peptides, proteins and/or antibodies are of use for therapy of cancer. Examples of cancers include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or treat malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected and/or treated include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

The exemplary conditions listed above that may be treated are not limiting. The skilled artisan will be aware that antibodies, antibody fragments or targeting peptides are known for a wide variety of conditions, such as autoimmune disease, graft-versus-host-disease, organ transplant rejection, cardiovascular disease, neurodegenerative disease, metabolic disease, cancer, infectious disease and hyperproliferative disease.

Exemplary autoimmune diseases include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

Kits

Various embodiments may concern kits containing components suitable for treating diseased tissue in a patient. Exemplary kits may contain at least one conjugated antibody or other targeting moiety as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

Example 1

Preparation of Dock-and-Lock (DNL) Constructs

DDD and AD Fusion Proteins

The DNL technique can be used to make dimers, trimers, tetramers, hexamers, etc. comprising virtually any antibody, antibody fragment, or other effector moiety. For certain preferred embodiments, the antibodies and antibody fragments may be produced as fusion proteins comprising either a dimerization and docking domain (DDD) or anchoring domain (AD) sequence. However, the skilled artisan will realize that other methods of conjugation exist, such as chemical cross-linking, click chemistry reaction, etc.

The technique is not limiting and any protein or peptide of use may be produced as an AD or DDD fusion protein for incorporation into a DNL construct. Where chemical cross-linking is utilized, the AD and DDD conjugates may comprise any molecule that may be cross-linked to an AD or DDD sequence using any cross-linking technique known in the art.

In certain exemplary embodiments, a dendrimer or other polymeric moiety such as polyethylene glycol (PEG) may be incorporated into a DNL construct, as described in further detail below.

For different types of DNL constructs, different AD or DDD sequences may be utilized. Exemplary DDD and AD sequences are provided below.

```
DDD1:
                                          (SEQ ID NO: 33)
SHIQIPPGLTELLQGYTVEVLRQQPPDLVEFAVEYFTRLREARA

DDD2:
                                          (SEQ ID NO: 34)
CGHIQIPPGLTELLQGYTVEVLRQQPPDLVEFAVEYFTRLREARA

AD1:
                                          (SEQ ID NO: 35)
QIEYLAKQIVDNAIQQA

AD2:
                                          (SEQ ID NO: 36)
CGQIEYLAKQIVDNAIQQAGC
```

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                          (SEQ ID NO: 37)
SLRECELYVQKHNIQALLKDSIVQLCTARPERPMAFLREYFERLEKEE
AK

DDD3C
                                          (SEQ ID NO: 38)
MSCGGSLRECELYVQKHNIQALLKDSIVQLCTARPERPMAFLREYFER
LEKEEAK

AD3
                                          (SEQ ID NO: 39)
CGFEELAWKIAKMIWSDVFQQGC
```

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

```
                                          (SEQ ID NO: 40)
GSGGGGSGGGGSHIQIPPGLTELLQGYTVEVLRQQPPDLVEFAVEYFT
RLREARA
```

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

```
GSGGGGSGGGGSQIEYLAKQIVDNAIQQA    (SEQ ID NO: 41)
```

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2h

679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD 1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA 19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

Construction of N-DDD 1-Fd-hMN-14-pdHL2

N-DDD1-Fd-hMN-14-pdHL2 is an expression vector for production of a stable dimer that comprises two copies of a fusion protein N-DDD1-Fab-hMN-14, in which DDD1 is linked to hMN-14 Fab at the amino terminus of VH via a flexible peptide spacer. The expression vector was engineered as follows. The DDD1 domain was amplified by PCR.

As a result of the PCR, an NcoI restriction site and the coding sequence for part of the linker containing a BamHI restriction were appended to the 5' and 3' ends, respectively. The 170 bp PCR amplimer was cloned into the pGemT vector and clones were screened for inserts in the T7 (5') orientation. The 194 bp insert was excised from the pGemT vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR. As a result of the PCR, a BamHI restriction site and the coding sequence for part of the linker were appended to the 5' end of the amplimer. A stop codon and EagI restriction site was appended to the 3' end. The 1043 bp amplimer was cloned into pGemT. The hMN-14-Fd insert was excised from pGemT with BamHI and EagI restriction enzymes and then ligated with DDD1-SV3 vector, which was prepared by digestion with those same enzymes, to generate the construct N-DDD1-hMN-14Fd-SV3.

The N-DDD1-hMN-14 Fd sequence was excised with XhoI and EagI restriction enzymes and the 1.28 kb insert fragment was ligated with a vector fragment that was prepared by digestion of C-hMN-14-pdHL2 with those same enzymes. The final expression vector was N-DDD1-Fd-hMN-14-pDHL2. The N-linked Fab fragment exhibited similar DNL complex formation and antigen binding characteristics as the C-linked Fab fragment (not shown).

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchoring domain sequence of AD2 appended to the carboxyl terminal end of the CH 1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 2

Generation of TF1 DNL Construct

A large scale preparation of a DNL construct, referred to as TF1, was carried out as follows. N-DDD2-Fab-hMN-14 (Protein L-purified) and h679-Fab-AD2 (IMP-291-purified) were first mixed in roughly stoichiometric concentrations in 1 mM EDTA, PBS, pH 7.4. Before the addition of TCEP, SE-HPLC did not show any evidence of $a_2b$ formation (not shown). Instead there were peaks representing $a_4$ (7.97 min; 200 kDa), $a_2$ (8.91 min; 100 kDa) and B (10.01 min; 50 kDa). Addition of 5 mM TCEP rapidly resulted in the formation of the $a_2b$ complex as demonstrated by a new peak at 8.43 min, consistent with a 150 kDa protein (not shown). Apparently there was excess B in this experiment as a peak attributed to h679-Fab-AD2 (9.72 min) was still evident yet no apparent peak corresponding to either $a_2$ or $a_4$ was observed. After reduction for one hour, the TCEP was removed by overnight dialysis against several changes of PBS. The resulting solution was brought to 10% DMSO and held overnight at room temperature.

When analyzed by SE-HPLC, the peak representing $a_2b$ appeared to be sharper with a slight reduction of the retention time by 0.1 min to 8.31 min (not shown), which, based on our previous findings, indicates an increase in binding affinity. The complex was further purified by IMP-291 affinity chromatography to remove the kappa chain contaminants. As expected, the excess h679-AD2 was co-purified and later removed by preparative SE-HPLC (not shown).

TF1 is a highly stable complex. When TF1 was tested for binding to an HSG (IMP-239) sensorchip, there was no apparent decrease of the observed response at the end of sample injection. In contrast, when a solution containing an equimolar mixture of both C-DDD1-Fab-hMN-14 and h679-Fab-AD1 was tested under similar conditions, the observed increase in response units was accompanied by a detectable drop during and immediately after sample injection, indicating that the initially formed $a_2b$ structure was unstable. Moreover, whereas subsequent injection of WI2 gave a substantial increase in response units for TF1, no increase was evident for the C-DDD1/AD1 mixture.

The additional increase of response units resulting from the binding of WI2 to TF1 immobilized on the sensorchip corresponds to two fully functional binding sites, each contributed by one subunit of N-DDD2-Fab-hMN-14. This was confirmed by the ability of TF1 to bind two Fab fragments of WI2 (not shown). When a mixture containing h679-AD2 and N-DDD1-hMN14, which had been reduced and oxidized exactly as TF1, was analyzed by BIAcore, there was little additional binding of WI2 (not shown), indicating that a disulfide-stabilized $a_2b$ complex such as TF1 could only form through the interaction of DDD2 and AD2.

Two improvements to the process were implemented to reduce the time and efficiency of the process. First, a slight molar excess of N-DDD2-Fab-hMN-14 present as a mixture of $a_4/a_2$ structures was used to react with h679-Fab-AD2 so that no free h679-Fab-AD2 remained and any $a_4/a_2$ structures not tethered to h679-Fab-AD2, as well as light chains, would be removed by IMP-291 affinity chromatography. Second, hydrophobic interaction chromatography (HIC) has replaced dialysis or diafiltration as a means to remove TCEP following reduction, which would not only shorten the process time but also add a potential viral removing step. N-DDD2-Fab-hMN-14 and 679-Fab-AD2 were mixed and reduced with 5 mM TCEP for 1 hour at room temperature. The solution was brought to 0.75 M ammonium sulfate and then loaded onto a Butyl FF HIC column. The column was washed with 0.75 M ammonium sulfate, 5 mM EDTA, PBS to remove TCEP. The reduced proteins were eluted from the HIC column with PBS and brought to 10% DMSO. Following incubation at room temperature overnight, highly purified TF1 was isolated by IMP-291 affinity chromatography (not shown). No additional purification steps, such as gel filtration, were required.

Example 3

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 4

Production of TF10 Bispecific Antibody

A similar protocol was used to generate a trimeric TF10 DNL construct, comprising two copies of a C-DDD2-Fab-hPAM4 and one copy of C-AD2-Fab-679. The cancer-targeting antibody component in TF10 was derived from hPAM4, a humanized anti-pancreatic cancer mucin MAb that has been studied in detail as a radiolabeled MAb (e.g., Gold et al., *Clin. Cancer Res.* 13: 7380-7387, 2007). The hapten-binding component was derived from h679, a humanized anti-histaminyl-succinyl-glycine (HSG) MAb. The TF10 bispecific ([hPAM4]$_2$ x h679) antibody was produced using the method disclosed for production of the (anti CEA)$_2$ x anti HSG bsAb TF2, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

The skilled artisan will realize that the DNL techniques disclosed above may be used to produce complexes comprising any combination of antibodies, immunoconjugates, or other effector moieties that may be attached to an AD or DDD moiety.

Example 5

Production of AD- and DDD-Linked Fab and IgG Fusion Proteins from Multiple Antibodies Using the techniques described in the preceding Examples, the IgG and Fab fusion proteins shown in Table 2 were constructed and incorporated into DNL constructs. The fusion proteins retained the antigen-binding characteristics of the parent antibodies and the DNL constructs exhibited the antigen-binding activities of the incorporated antibodies or antibody fragments.

Example 6

Sequence Variants for DNL

In certain preferred embodiments, the AD and DDD sequences incorporated into the DNL construct comprise the amino acid sequences of AD1, AD2, AD3, DDD1, DDD2, DDD3 or DDD3C as discussed above. However, in alternative embodiments sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 42)
SLRECELYVQKHNIQALLKDVSIVQLCTARPERPMAFLREYFEKLEKE
EAK

TABLE 2

| Fusion Protein | Binding Specificity |
|---|---|
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |

TABLE 2-continued

| Fusion Protein | Binding Specificity |
|---|---|
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

PKA RIβ
(SEQ ID NO: 43)
SLKGCELYVQLHGIQQVLKDCIVHLCISKPERPMKFLREHFEKLEKEE
NRQILA

PKA RIIα
(SEQ ID NO: 44)
SHIQIPPGLTELLQGYTVEVGQQPPDLVDFAVEYFTRLREARRQ

PKA RIIβ
(SEQ ID NO: 45)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Can et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:33 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 33)
SHIQIPPGLTELLQGYTVEVLRQQPPDLVEFAVEYFTRLREARA

Alto et al. (2003) performed a bioinformatic analysis of the AD sequence of various AKAP proteins to design an RII selective AD sequence called AKAP-IS (SEQ ID NO:35), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:35. The skilled artisan will realize that in designing sequence variants of the AD sequence, one would desirably avoid changing any of the underlined residues, while conservative amino acid substitutions might be made for residues that are less critical for DDD binding.

```
AKAP-IS SEQUENCE
QIEYLAKQIVDNAIQQA         (SEQ ID NO: 35)
```

Gold (2006) utilized crystallography and peptide screening to develop a SuperAKAP-IS sequence (SEQ ID NO:46), exhibiting a five order of magnitude higher selectivity for the RII isoform of PKA compared with the R1 isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:47-49. Substitutions relative to the AKAP-IS sequence are underlined. It is anticipated that, as with the AD2 sequence shown in SEQ ID NO:46, the AD moiety may also include the additional N-terminal residues cysteine and glycine and C-terminal residues glycine and cysteine.

```
SuperAKAP-IS
QIEYVAKQIVDYAIHQA         (SEQ ID NO: 46)

Alternative AKAP sequences
QIEYKAKQIVDHAIHQA         (SEQ ID NO: 47)

QIEYHAKQIVDHAIHQA         (SEQ ID NO: 48)

QIEYVAKQIVDHAIHQA         (SEQ ID NO: 49)
```

Figure 2:
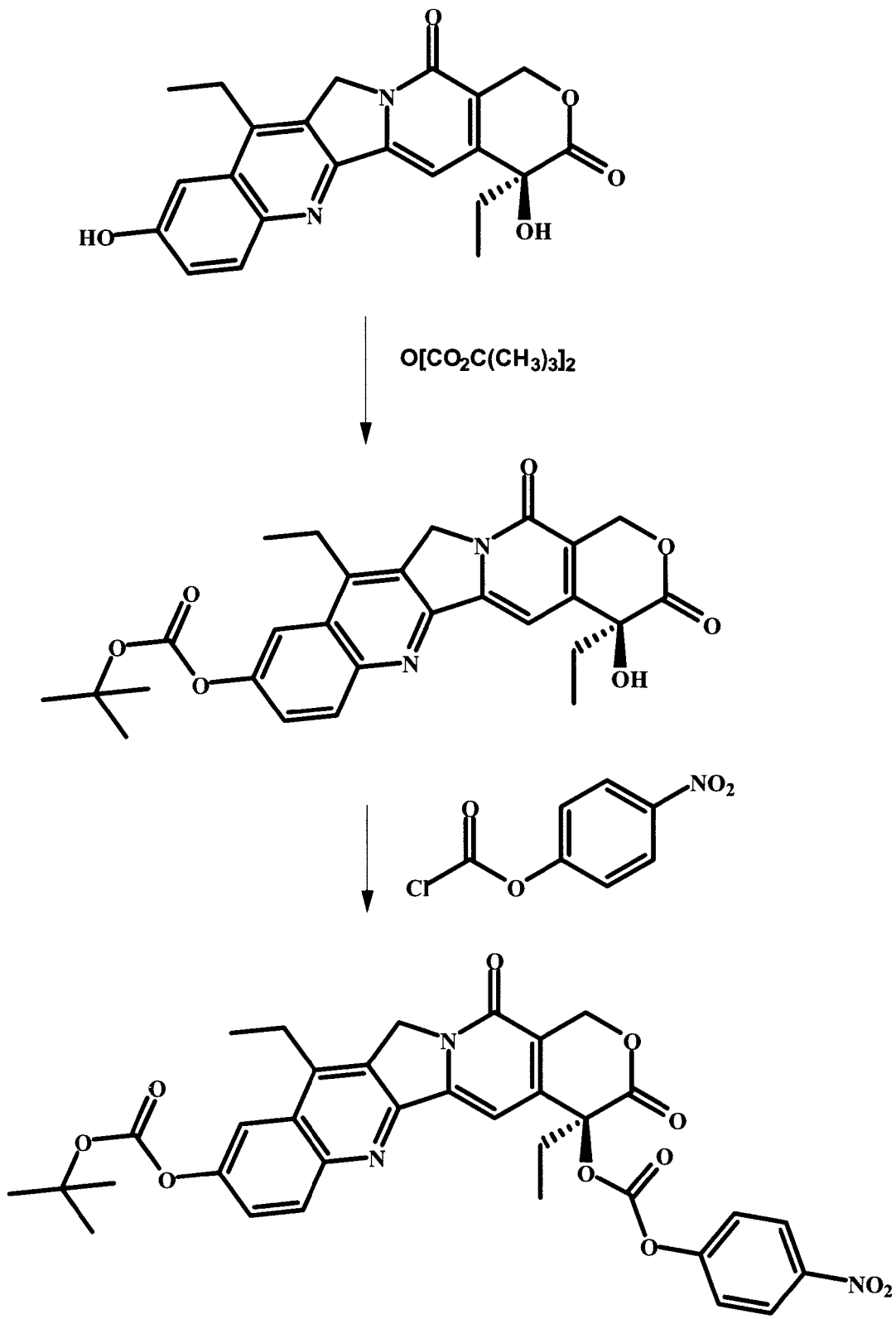
FIG. 2. Activation of SN-38 for peptide conjugation.

FIG. 2 of Gold et al. disclosed additional DDD-binding sequences from a variety of AKAP proteins, shown below.

```
RII-Specific AKAPs
AKAP-KL
PLEYQAGLLVQNAIQQAI        (SEQ ID NO: 50)

AKAP79
LLIETASSLVKNAIQLSI        (SEQ ID NO: 51)

AKAP-Lbc
LIEEAASRIVDAVIEQVK        (SEQ ID NO: 52)

RI-Specific AKAPs
AKAPce
ALYQFADRFSELVISEAL        (SEQ ID NO: 53)

RIAD
LEQVANQLADQIIKEAT         (SEQ ID NO: 54)

PV38
FEELAWKIAKMIWSDVF         (SEQ ID NO: 55)

Dual-Specificity AKAPs
AKAP7
ELVRLSKRLVENAVLKAV        (SEQ ID NO: 56)

MAP2D
TAEEVSARIVQVVTAEAV        (SEQ ID NO: 57)

DAKAP1
QIKQAAFQLISQVILEAT        (SEQ ID NO: 58)

DAKAP2
LAWKIAKMIVSDVMQQ          (SEQ ID NO: 59)
```

Stokka et al. (2006) also developed peptide competitors of AKAP binding to PKA, shown in SEQ ID NO:60-62. The peptide antagonists were designated as Ht31 (SEQ ID NO:60), RIAD (SEQ ID NO:61) and PV-38 (SEQ ID NO:62). The Ht-31 peptide exhibited a greater affinity for the RII isoform of PKA, while the RIAD and PV-38 showed higher affinity for R1.

```
Ht31
DLIEEAASRIVDAVIEQVKAAGAY  (SEQ ID NO: 60)

RIAD
LEQYANQLADQIIKEATE        (SEQ ID NO: 61)

PV-38
FEELAWKIAKMIWSDVFQQC      (SEQ ID NO: 62)
```

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

| AKAP Peptide sequences | |
|---|---|
| | Peptide Sequence |
| AKAPIS | QIEYLAKQIVDNAIQQA (SEQ ID NO: 35) |
| AKAPIS-P | QIEYLAKQIPDNAIQQA (SEQ ID NO: 63) |
| Ht31 | KGADLIEEAASRIVDAVIEQVKAAG (SEQ ID NO: 64) |
| Ht31-P | KGADLIEEAASRIPDAPIEQVKAAG (SEQ ID NO: 65) |
| AKAP7δ-wt-pep | PEDAELVRLSKRLVENAVLKAVQQY (SEQ ID NO: 66) |
| AKAP7δ-L304T-pep | PEDAELVRTSKRLVENAVLKAVQQY (SEQ ID NO: 67) |
| AKAP7δ-L308D-pep | PEDAELVRLSKRDVENAVLKAVQQY (SEQ ID NO: 68) |
| AKAP7δ-P-pep | PEDAELVRLSKRLPENAVLKAVQQY (SEQ ID NO: 69) |
| AKAP7δ-PP-pep | PEDAELVRLSKRLPENAPLKAVQQY (SEQ ID NO: 70) |
| AKAP7δ-L314E-pep | PEDAELVRLSKRLVENAVEKAVQQY (SEQ ID NO: 71) |
| AKAP1-pep | EEGLDRNEEIKRAAFQIISQVISEA (SEQ ID NO: 72) |

TABLE 3-continued

AKAP Peptide sequences

| | Peptide Sequence |
|---|---|
| AKAP2-pep | LVDDPLEYQAGLLVQNAIQQAIAEQ (SEQ ID NO: 73) |
| AKAP5-pep | QYETLLIETASSLVKNAIQLSIEQL (SEQ ID NO: 74) |
| AKAP9-pep | LEKQYQEQLEEEVAKVIVSMSIAFA (SEQ ID NO: 75) |
| AKAP10-pep | NTDEAQEELAWKIAKMIVSDIMQQA (SEQ ID NO: 76) |
| AKAP11-pep | VNLDKKAVLAEKIVAEAIEKAEREL (SEQ ID NO: 77) |
| AKAP12-pep | NGILELETKSSKLVQNIIQTAVDQF (SEQ ID NO: 78) |
| AKAP14-pep | TQDKNYEDELTQVALALVEDVINYA (SEQ ID NO: 79) |
| Rab32-pep | ETSAKDNINIEEAARFLVEKILVNH (SEQ ID NO: 80) |

Residues that were highly conserved among the AD domains of different AKAP proteins are indicated below by underlining with reference to the AKAP IS sequence (SEQ ID NO:35). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
AKAP-IS
QIEYLAKQIVDNAIQQA        (SEQ ID NO: 35)
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:33. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 33)
SHI*QIPP*GLT*ELLQGYT*V*EVLRQQPP*DLVE*FAVE*YF*TR*LREA*RA

The skilled artisan will realize that these and other amino acid substitutions in the antibody moiety or linker portions of the DNL constructs may be utilized to enhance the therapeutic and/or pharmacokinetic properties of the resulting DNL constructs.

Example 7

Antibody-Dendrimer DNL Complex

We synthesized and characterized a novel immunoconjugate, designated E1-05/2, which was made by the DNL method to comprise half of a generation 5 (G5) PAMAM dendrimer (G5/2) site-specifically linked to a stabilized dimer of Fab derived from hRS7, a humanized antibody that is rapidly internalized upon binding to the Trop-2 antigen expressed on various solid cancers.

Methods

E1-G5/2 was prepared by combining two self-assembling modules, AD2-G5/2 and hRS7-Fab-DDD2, under mild redox conditions, followed by purification on a Protein L column. To make AD2-G5/2, we derivatized the AD2 peptide with a maleimide group to react with the single thiol generated from reducing a G5 PAMAM with a cystamine core and used reversed-phase HPLC to isolate AD2-G5/2. We produced hRS7-Fab-DDD2 as a fusion protein in myeloma cells, as described in the Examples above.

The molecular size, purity and composition of E1-G5/2 were analyzed by size-exclusion HPLC, SDS-PAGE, and Western blotting. The biological functions of E1-G5/2 were assessed by binding to an anti-idiotype antibody against hRS7, a gel retardation assay, and a DNase protection assay.

Results

E1-G5/2 was shown by size-exclusion HPLC to consist of a major peak (>90%) flanked by several minor peaks. The three constituents of E1-G5/2 (Fd-DDD2, the light chain, and AD2-G5/2) were detected by reducing SDS-PAGE and confirmed by Western blotting. Anti-idiotype binding analysis revealed E1-G5/2 contained a population of antibody-dendrimer conjugates of different size, all of which were capable of recognizing the anti-idiotype antibody, thus suggesting structural variability in the size of the purchased G5 dendrimer.

CONCLUSION

The DNL technique can be used to build dendrimer-based nanoparticles that are targetable with antibodies. Such agents have improved properties as carriers of drugs, plasmids or siRNAs for applications in vitro and in vivo.

Example 8

Maleimide AD2 Conjugate for DNL Dendrimers

IMP 498 (SEQ ID NO:83)

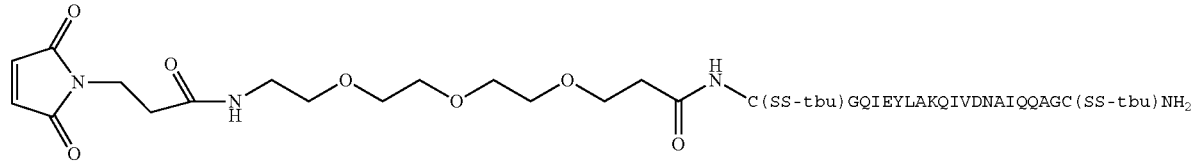

The peptide IMP 498 up to and including the PEG moiety was synthesized on a Protein Technologies PS3 peptide synthesizer by the Fmoc method on Sieber Amide resin (0.1 mmol scale). The maleimide was added manually by mixing the β-maleimidopropionic acid NHS ester with diisopropylethylamine and DMF with the resin for 4 hr. The peptide was cleaved from the resin with 15 mL TFA, 0.5 mL $H_2O$, 0.5 mL triisopropylsilane, and 0.5 mL thioanisole for 3 hr at room temperature. The peptide was purified by reverse phase HPLC using $H_2O/CH_3CN$ TFA buffers to obtain about 90 mg of purified product after lyophilization.

Synthesis of Reduced G5 Dendrimer (G5/2)

The G-5 dendrimer (10% in MeOH, Dendritic Nanotechnologies), 2.03 g, $7.03 \times 10^{-6}$ mol was reduced with 0.1426 TCEP.HCl 1:1 MeOH/$H_2O$ (~4 mL) and stirred overnight at room temperature. The reaction mixture was purified by reverse phase HPLC on a C-18 column eluted with 0.1% TFA $H_2O/CH_3CN$ buffers to obtain 0.0633 g of the desired product after lyophilization.

Synthesis of G5/2 Dendrimer-AD2 Conjugate

The G5/2 Dendrimer, 0.0469 g ($3.35 \times 10^{-6}$ mol) was mixed with 0.0124 g of IMP 498 ($4.4 \times 10^{-6}$ mol) and dissolved in 1:1 MeOH/1M $NaHCO_3$ and mixed for 19 hr at room temperature followed by treatment with 0.0751 g dithiothreitol and 0.0441 g TCEP HCl. The solution was mixed overnight at room temperature and purified on a C4 reverse phase HPLC column using 0.1% TFA $H_2O/CH_3CN$ buffers to obtain 0.0033 g of material containing the conjugated AD2 and dendrimer as judged by gel electrophoresis and Western blot.

Example 9

Delivery System for Cytotoxic Drugs Via Bispecific Antibody Pretargeting

As discussed above, pretargeting methods have been used with bispecific antibodies and targetable constructs for improved targeted delivery of therapeutic agents with decreased systemic toxicity. In pretargeting, the bispecific antibody (bsMAb) is administered first to the subject and allowed to localize to a targeted cell or tissue. Optionally, a clearing agent may be administered to expedite clearance of the bsMAb from circulation. After the bsMAb has cleared from circulation, a targetable construct is administered that binds to the bsMAb localized in the target tissue. The targetable construct is conjugated to one or more therapeutic and/or diagnostic agents. Because the targetable construct clears very rapidly from circulation and is typically excreted intact, primarily in the urine, the cytotoxic therapeutic agent spends little time in circulation and is not taken up by non-targeted tissues, thus reducing systemic toxicity.

The object of the present Example was to develop novel reagents for use in therapeutic pretargeting. These were tested in an animal model for human colorectal cancer, using an anti-carcinoembryonic antigen (CEACAM5) bispecific antibody. An exemplary cytotoxic drug used in the pretargeting study was SN-38.

A core peptide targetable construct, described in detail below (IMP 453), was developed. The targetable construct was modified to attach SN-38 and can attach up to 4 SN-38 moieties per core peptide. A dendron polymer was also prepared that can bind 8 to 16 SN-38 moieties per polymer molecule. The targetable construct has the ability to bind both therapeutic radionuclides and chemotherapeutic agents for combination therapy of diseased tissues, such as cancer.

An exemplary bispecific antibody used was the TF2 DNL construct, described in the Examples above. TF2 contains two CEACAM5-binding hMN-14 Fab moieties and one HSG-binding h679 Fab moiety. The targetable construct contained two HSG haptens per peptide to allow cross-linking of two TF2 bsMAbs at the tumor surface. Cross-linking of the two bispecific antibodies enhances the retention of pretargeted peptide on the tumor surface (Barbet et al., 1999, Cancer Biother Radiopharm 14:153-66).

Preferably, the peptide-drug conjugates are designed to allow for the slow release of the drug, for example with a drug linkage that is stable for up to 1 day, but then released in a time-dependent manner. This matches the kinetics of pretargeting, where the peptide reaches maximum accumulation in the tumor within 1 h, and over the next few hours over 90% is cleared from the bloodstream by urinary excretion. Unlike direct drug-antibody conjugates that are retained in the body for sustained periods, allowing catabolism in the liver and other organs, in pretargeting most of the injected product is excreted intact to minimize systemic side effects. But the drug-peptide conjugate localized in the tumor is slowly released within the tumor.

Synthesis of Targetable Construct Peptides

Peptides were synthesized by solid phase peptide synthesis using a combination of Aloc and Fmoc protecting groups to allow selective modification of peptide side chains and elongation of the peptide during peptide synthesis. IMP 402 was initially synthesized and used to make IMP 453, according to FIG. 1. IMP 402 is also suitable for conjugation to a dendron drug carrier.

IMP 402 was synthesized on Sieber amide resin as follows. Aloc-D-Lys(Fmoc)-OH was attached to the resin. The lysine side chain Fmoc was removed and the N-Trityl-histaminyl-succinyl-glycyl group (Trityl-HSG-OH) was attached. The Aloc group was removed from the lysine and the Fmoc-D-Tyr(But)-OH was added to the peptide. Another Aloc-D-Lys (Fmoc)-OH was added to the peptide and the Trityl-HSG-OH group was added to that lysine side chain. The Aloc group was removed from the lysine and Fmoc-D-Ala-OH, Fmoc-D-Cys (Trt)-OH and Tri-t-butyl-DOTA-OH were added to the peptide using standard peptide coupling methods. The peptide was cleaved from the resin and purified by HPLC.

Synthesis of Peptide Drug Conjugates

The synthesis of the SN-38 precursor needed for peptide coupling is shown in FIG. 2. The 10 position of SN-38 was first protected with a Boc group and the 20 position was then modified with p-nitrophenyl chloroformate to produce the 10-Boc-20-p-nitrophenylcarbonate SN-38 precursor. The activated SN-38 was then mixed with the peptide to produce the Boc-SN-38 protected conjugate, which was purified by HPLC. The Boc group was then removed under mild conditions to produce the desired product in 20% overall yield for the whole conjugation process. The resulting SN-38-conjugated peptide IMP 453 contains one DOTA, one SN-38 and two HSG moieties.

An initial study with $^{111}$In-labeled IMP 453 showed excellent tumor targeting to the LS174 human colon cancer cell line (28% ID/g) (Table 4). Most of the peptide was cleared by urinary excretion (Table 4). Renal uptake at 3 hr was elevated (21% ID/g), higher than was observed with bis-DTPA peptides (not shown), but 50% of the initial kidney uptake was eliminated by 24 hr. When the peptide was injected in mice that did not receive bispecific antibody, kidney uptake was only 9.97% ID/g (Table 5). The higher uptake in the kidneys of pretargeted mice is probably due the presence of bispecific antibody in the blood or kidney. Modification of the peptide to contain a DTPA instead of DOTA chelating moiety may reduce kidney uptake, to the same range as seen with bis-DTPA peptides like IMP 225 and IMP 274. In the absence of TF2, there was little uptake of labeled peptide into the tumor (Table 5).

TABLE 4

$^{111}$In IMP 453 biodistribution in scLS174T tumor-bearing nude mice pretargeted with TF2. Tissue uptake shown as % ID/g.

| Tissue | 3 Hr | 24 Hr | 48 Hr |
| --- | --- | --- | --- |
| Tumor | 28.32 ± 4.03 | 15.44 ± 1.18 | 9.69 ± 1.97 |
| Liver | 0.56 ± 0.08 | 0.53 ± 0.19 | 0.36 ± 0.06 |
| Spleen | 0.37 ± 0.11 | 0.66 ± 0.89 | 0.25 ± 0.07 |
| Kidney | 21.10 ± 4.14 | 10.00 ± 2.45 | 7.11 ± 1.17 |
| Lung | 0.56 ± 0.10 | 0.18 ± 0.07 | 0.14 ± 0.03 |
| Blood | 0.29 ± 0.03 | 0.09 ± 0.04 | 0.04 ± 0.01 |
| Stomach | 0.41 ± 0.33 | 0.20 ± 0.12 | 0.07 ± 0.01 |
| Sm. Int. | 0.68 ± 0.45 | 0.22 ± 0.09 | 0.12 ± 0.03 |
| Lg. Int. | 1.23 ± 1.41 | 0.23 ± 0.05 | 0.16 ± 0.07 |

TABLE 5

$^{111}$In IMP 453 biodistribution in scLS174T tumor-bearing nude mice without bsMAb.

| Tissue | 3 Hr |
| --- | --- |
| Tumor | 0.37 ± 0.09 |
| Liver | 0.37 ± 0.18 |
| Spleen | 0.22 ± 0.07 |
| Kidney | 9.97 ± 0.94 |
| Lung | 0.31 ± 0.14 |
| Blood | 0.24 ± 0.01 |
| Stomach | 0.11 ± 0.06 |
| Sm. Int. | 0.20 ± 0.10 |
| Lg. Int. | 0.52 ± 0.27 |

DTPA Conjugated Peptide

An analog of IMP 453 is synthesized as described above, with the DOTA group replaced by a DTPA group. The peptide is labeled with $^{111}$In and the tumor targeting and clearance of the peptide is examined in LSI 74T tumor-bearing nude mice. The peptide shows targeting in vivo that is similar to the DOTA labeled peptide, but with lower renal uptake at 3 hours. The peptide toxicity is formulated in an acetate buffer between pH 5-6 with an excipient added and lyophilized for therapeutic use.

Dendron Conjugation

Figure 3:
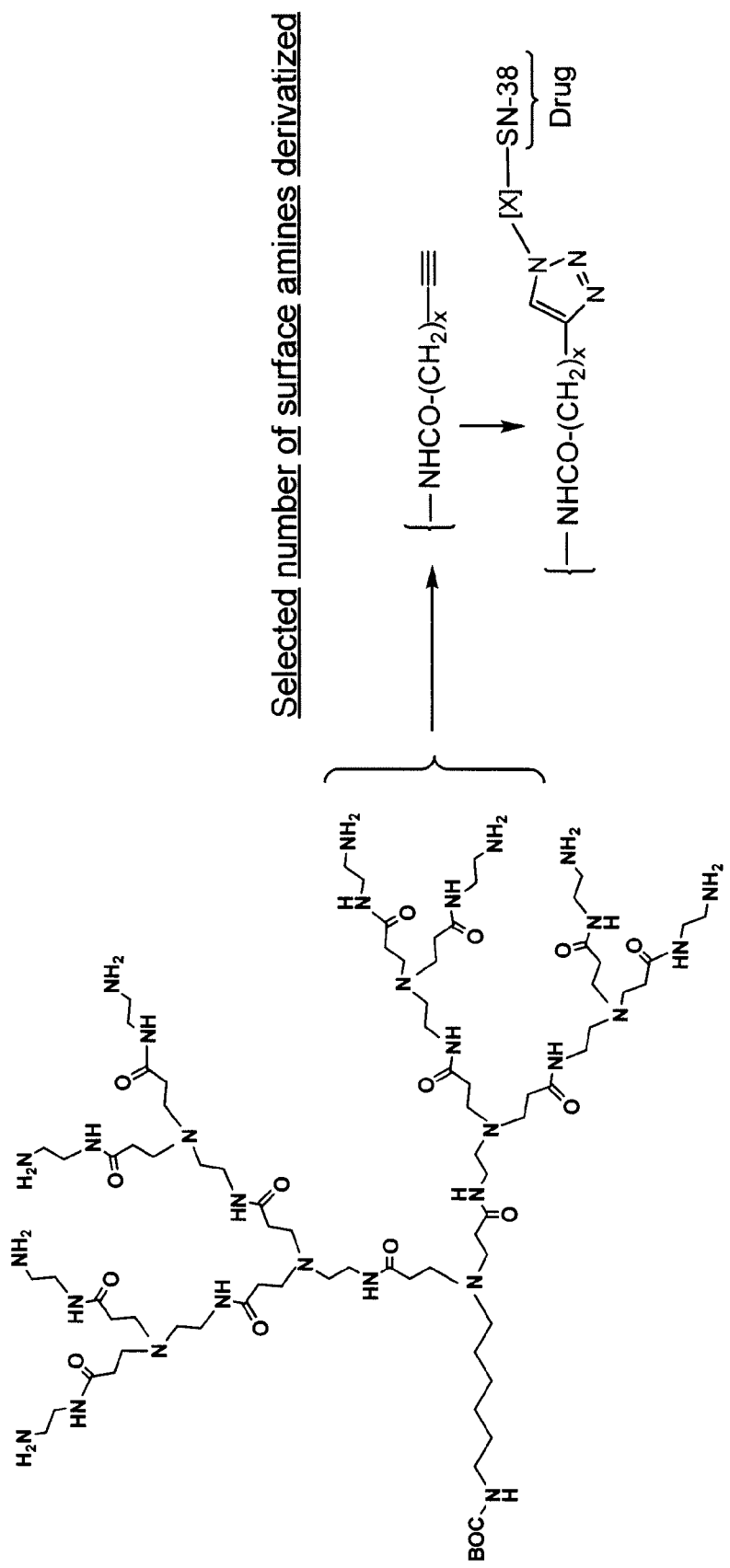
FIG. 3. Dendron carrier for SN-38.

The advantage of a dendron carrier molecule is that it is asymmetrical, with surface groups and a focal functional group for differential substitutions. Attachment of the bis-HSG peptide at the defined focal site results in site-specific placement. A PAMAM dendron is exemplified in FIG. 3, although other dendrons may be used with up to sixteen surface groups. Briefly, this involves multiple derivatizations with acetylene groups for introducing multiple molecules of SN-38 via azide-yne click cycloaddition, as discussed above.

The focal functional group is transformed by 'BOC' deprotection and derivatization to a maleimide, which is conjugated to a cysteine-containing-bis-HSG peptide for pretargeting. The same peptide also contains a DOTA molecule that will enable labeling with In-111 radiolabel for determining in vivo targeting. Dendron with either amino group or some other group on the surface is purchased if found to be cost effective. Alternatively, the dendron specified is made in-house by an iterative sequence of methacrylate reaction and ethylene diamine-based esterolysis, starting with mono-protected 1,6-diaminohexane. The BOC-protected amino group serves as the focal functional group that will ultimately carry the bis-HSG peptide site-selectively.

Azido-SN-38 Preparation

Figure 4:
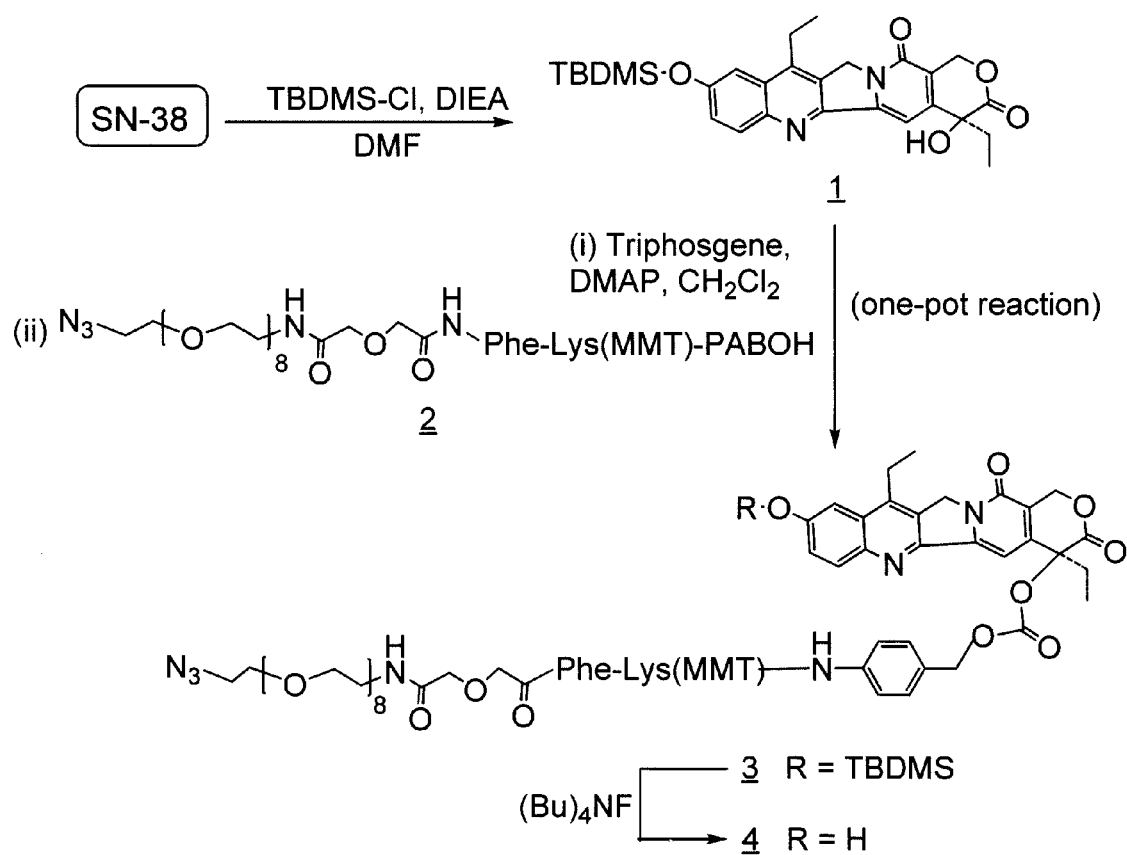
FIG. 4. Synthesis of azido-SN-38 for attachment to dendron.

For click chemistry reactions, such as the click chemistry addition of SN-38 to a targetable construct, an azido-SN-38 moiety may be prepared to react with a cyclooctyne or alkyne moiety on the targetable construct. An exemplary preparation is shown in FIG. 4. SN-38 silyl ether (intermediate 1) has been prepared in a number of small scale reactions as well as in one large scale reaction, using 3.43 g SN-38 with reproducibly >74% yield. The carbonate (intermediate 3) was prepared five times, using cross-linker as a limiting reagent in quantities in the range of 0.24-2.0 g, to obtain the purified carbonate in 0.33-2.63 g (77-90%). At this stage, deblocking of silyl group was effected and the material was purified by a simple aqueous work-up that ensured the removal of the fluoride reagent. The azido-SN-38, which is intermediate 4 in FIG. 4, is used for click cycloaddition to acetylene groups on the dendrimer.

The click cycloaddition has been simplified from that published (Moon et al., 2008, Chemotherapy. Med. Chem. 51: 6916-6926) by resorting to a homogeneous reaction in dichloromethane using triphenylphosphine and cuprous bromide in 0.1 to 0.2 equivalents, with attendant improvements in the quality and the yield of the product. With the old method, the yield was 58-82%, while with the new method, it was 86%. We believe this new process is amenable to easy scale-up in view of the homogeneous reaction condition. The final reaction in the synthetic sequence is the removal of 'MMT' group using a mild acid, such as dichloroacetic acid, which proceeds in a high yield. The click cycloaddition will also be examined in aqueous reaction condition involving copper sulfate and ascorbate, using DMSO as cosolvent.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

What is claimed is:

1. A composition comprising DOTA-D-Cys-D-Ala-D-Lys(HSG)-D-Tyr-D-Lys(HSG)-NH$_2$ (IMP 402) wherein the D-Cys residue of IMP 402 is conjugated to SN-38 by a thiocarbonate linkage.

2. A composition comprising DOTA-D-Cys-D-Ala-D-Lys(HSG)-D-Tyr-D-Lys(HSG)-NH$_2$ (IMP 402) wherein the D-Cys residue of IMP 402 is conjugated to a dendron.

3. The composition according to claim 2, wherein 4 to 16 copies of a therapeutic agent are conjugated to the dendron.

4. The composition according to claim 3, wherein the therapeutic agent is selected from the group consisting of a toxin, drug, radionuclide, immunomodulator, cytokine, lymphokine, chemokine, growth factor, tumor necrosis factor, hormone, enzyme, oligonucleotide, photoactive therapeutic agent, anti-angiogenic agent and pro-apoptotic agent.

5. The composition according to claim 3, wherein the therapeutic agent is a camptothecin.

6. The composition according to claim 3, wherein the therapeutic agent is SN-38.

7. The composition according to claim 3, wherein the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

8. The composition of claim 4, wherein the drug is selected from the group consisting of nitrogen mustard, ethylenimine derivative, alkyl sulfonate, nitrosourea, gemcitabine, triazene, folic acid analog, anthracycline, taxane, COX-2 inhibitor, pyrimidine analog, purine analog, antibiotic, enzyme inhibitor, epipodophyllotoxin, platinum coordination complex, vinca alkaloid, substituted urea, methyl hydrazine derivative, adrenocortical suppressant, endostatin, taxol, camptothecin, SN-38, doxorubicin, doxorubicin analogs, antimetabolite, alkylating agent, antimitotic, anti-angiogenic agent, tyrosine kinase inhibitor, mTOR inhibitor, heat shock protein (HSP90) inhibitor, proteosome inhibitor, HDAC inhibitor, pro-apoptotic agent, methotrexate and CPT-11.

9. The composition of claim 4, wherein the toxin is selected from the group consisting of ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

10. The composition of claim 4, wherein the radionuclide is selected from the group consisting of $^{18}$F, $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{103m}$In, $^{119}$Sb, $^{11}$C, $^{121m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo and $^{99m}$Tc.

* * * * *